United States Patent
Hintzer et al.

(10) Patent No.: US 11,292,763 B2
(45) Date of Patent: Apr. 5, 2022

(54) METHODS OF MAKING A POLYFLUORINATED ALLYL ETHER AND COMPOUNDS RELATING TO THE METHODS

(71) Applicant: 3M INNOVATIVE PROPERTIES COMPANY, St. Paul, MN (US)

(72) Inventors: Klaus Hintzer, Kastl (DE); Markus E. Hirschberg, Mühldorf (DE); Romana Pajkert, Bremen (DE); Gerd-Volker Röschenthaler, Bremen (DE); Sergey N. Tverdomed, Bremen (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 226 days.

(21) Appl. No.: 16/613,900

(22) PCT Filed: May 17, 2018

(86) PCT No.: PCT/IB2018/053488
§ 371 (c)(1),
(2) Date: Nov. 15, 2019

(87) PCT Pub. No.: WO2018/211457
PCT Pub. Date: Nov. 22, 2018

(65) Prior Publication Data
US 2021/0276946 A1    Sep. 9, 2021

Related U.S. Application Data

(60) Provisional application No. 62/508,569, filed on May 19, 2017.

(51) Int. Cl.
*C07C 303/26* (2006.01)
*C07C 41/14* (2006.01)
*C07C 309/06* (2006.01)
*C07C 303/24* (2006.01)
*C07C 305/26* (2006.01)

(52) U.S. Cl.
CPC ............ *C07C 303/26* (2013.01); *C07C 41/14* (2013.01); *C07C 303/24* (2013.01); *C07C 305/26* (2013.01); *C07C 309/06* (2013.01)

(58) Field of Classification Search
CPC ..... C07C 303/26; C07C 41/14; C07C 309/06; C07C 303/24; C07C 305/26
See application file for complete search history.

(56) References Cited

U.S. PATENT DOCUMENTS

| | | | |
|---|---|---|---|
| 3,231,626 A | 1/1966 | Hauptschein | |
| 3,654,335 A * | 4/1972 | Young et al. | ......... C07C 303/24 558/46 |
| 4,273,728 A | 6/1981 | Krespan | |
| 4,273,729 A | 6/1981 | Krespan | |
| 4,275,225 A | 6/1981 | Krespan | |
| 4,292,449 A | 9/1981 | Krespan | |
| 4,349,650 A | 9/1982 | Krespan | |
| 4,384,128 A | 5/1983 | Krespan | |
| 4,423,197 A | 12/1983 | Behr | |
| 4,621,116 A | 11/1986 | Morgan | |
| 5,285,002 A | 2/1994 | Grootaert | |
| 5,378,782 A | 1/1995 | Grootaert | |
| 5,442,097 A | 8/1995 | Obermeier | |
| 5,463,021 A | 10/1995 | Beyer | |
| 5,891,965 A | 4/1999 | Worm | |
| 6,255,535 B1 | 7/2001 | Schulz | |
| 6,429,258 B1 | 8/2002 | Morgan | |
| 6,613,941 B1 | 9/2003 | Felix | |
| 6,706,193 B1 | 3/2004 | Burkard | |
| 6,794,550 B2 | 9/2004 | Hintzer | |
| 7,018,541 B2 | 3/2006 | Hintzer | |

(Continued)

FOREIGN PATENT DOCUMENTS

| | | |
|---|---|---|
| CN | 101696178 A | 4/2010 |
| CN | 101712639 A | 5/2010 |

(Continued)

OTHER PUBLICATIONS

Beeker, Gmelin Handbook of Inorganic Chemistry 8th Edition, B Boron Compounds 1st Supplement vol. 3, 45 (1981).
Booth, "The Synthesis of α-Amino-acids. Part I. dl-Methionine", *Journal of Chemical Society*, Jan. 1944, pp. 666-667.
Engelbrecht, Boron-tris(trifluoromethane-sulfonate), B(OSO&Fa)a, in Trifluoromethane SulPonic Acid—a New "Super Acid System", *Z. anorg. Allg. Chem.*, Aug. 1977, vol. 433, No. 1, pp. 19-25.
Kostov, "Study on the Synthesis of Perfluorovinyl-Sulfonic Functional Monomer and Its Copolymerization with Tetrafluoroethylene", Journal of Applied Polymer Science, 1993, vol. 47, pp. 735-741.
Krespan, "Perfluoroallyl Fluorosulfate, a Reactive New Perfluoroallylating Agent", *Journal of the American Chemical Society*, Sep. 1981, vol. 103, No. 18, pp. 5598-5599.
Mistry, "The Synthesis and Vibrational Spectra of Fluorosulfate Derivatives of Titanium, Zirconium and Hafnium", *Journal of Fluorine Chemistry*, 1994, vol. 68, No. 3, pp. 239-248.

(Continued)

*Primary Examiner* — Rosalynd A Keys
(74) *Attorney, Agent, or Firm* — Thomas M. Spielbauer

(57) ABSTRACT

A method includes combining first components including at least one of $CF_2=CF-CF_2-OSO_2Cl$ or $CF_2=CF-CF_2-OSO_2CF_3$, a polyfluorinated compound having at least one ketone or carboxylic acid halide, and fluoride ion to provide a compound comprising at least one perfluorinated allyl ether group. A method includes combining second components including $B(OSO_2Cl)_3$ and hexafluoropropylene to provide $CF_2=CF-CF_2-OSO_2Cl$. Another method includes combining second components including $M(OSO_2CF_3)_3$ and hexafluoropropylene at a temperature above 0° C. to provide $CF_2=CF-CF_2-OSO_2CF_3$, wherein M is Al or B. The compound $CF_2=CF-CF_2-OSO_2Cl$ is also provided.

18 Claims, No Drawings

(56) References Cited

U.S. PATENT DOCUMENTS

| | | |
|---|---|---|
| 7,560,517 B2 | 7/2009 | Hintzer |
| 7,671,112 B2 | 3/2010 | Hintzer |
| 7,989,552 B2 | 8/2011 | Grootaert |
| 8,227,139 B2 | 7/2012 | Watakabe |
| 8,470,943 B2 | 6/2013 | Watakabe |
| 8,633,328 B2 | 1/2014 | Zipplies |
| 8,906,821 B2 | 12/2014 | Grootaert |
| 9,139,668 B2 | 9/2015 | Zipplies |
| 9,156,926 B2 | 10/2015 | Lochhaas |
| 9,199,929 B2 | 12/2015 | Qiu |
| 9,556,298 B2 | 1/2017 | Hintzer |
| 9,688,796 B2 | 6/2017 | Hintzer |
| 9,711,816 B2 | 7/2017 | Lochhaas |
| 9,828,320 B2 | 11/2017 | Hintzer |
| 9,982,091 B2 | 5/2018 | Hintzer |
| 10,087,307 B2 | 10/2018 | Lochhaas |
| 10,087,322 B2 | 10/2018 | Chen |
| 10,093,820 B2 | 10/2018 | Zipplies |
| 10,189,927 B2 | 1/2019 | Ino |
| 10,227,484 B2 | 3/2019 | Chen |
| 10,557,031 B2 | 2/2020 | Aoki |
| 10,590,224 B2 | 3/2020 | Mitchell |
| 10,676,555 B2 | 6/2020 | Duchesne |
| 10,717,795 B2 | 7/2020 | Duchesne |
| 10,730,980 B2 | 8/2020 | Duchesne |
| 10,844,152 B2 | 11/2020 | Hintzer |
| 10,875,948 B2 | 12/2020 | Jochum |
| 10,927,235 B2 | 2/2021 | Fukushi |
| 11,028,198 B2 | 6/2021 | Kaspar |
| 2006/0199898 A1 | 9/2006 | Funaki |
| 2006/0223924 A1 | 10/2006 | Tsuda |
| 2006/0281946 A1 | 12/2006 | Morita |
| 2007/0015865 A1 | 1/2007 | Hintzer |
| 2007/0060699 A1 | 3/2007 | Tsuda |
| 2007/0117915 A1 | 5/2007 | Funaki |
| 2007/0142513 A1 | 6/2007 | Tsuda |
| 2007/0142541 A1 | 6/2007 | Hintzer |
| 2007/0149733 A1 | 6/2007 | Otsuka |
| 2010/0311906 A1 | 12/2010 | Lavallée |
| 2016/0115294 A1 | 4/2016 | Grooteart |
| 2016/0280824 A1 | 9/2016 | Hintzer |
| 2016/0347966 A1 | 12/2016 | Dadalas |
| 2018/0371121 A1 | 12/2018 | Hintzer |
| 2019/0027769 A1 | 1/2019 | Dahlke |
| 2019/0030794 A1 | 1/2019 | Jiang |
| 2019/0185599 A1 | 6/2019 | Hintzer |
| 2020/0055971 A1 | 2/2020 | Hintzer |
| 2021/0070686 A1 | 3/2021 | Berg |
| 2021/0108063 A1 | 4/2021 | Dadalas |

FOREIGN PATENT DOCUMENTS

| | | | |
|---|---|---|---|
| DE | 2753886 | 12/1977 | |
| EP | 0822175 | 2/1998 | |
| EP | 3059265 A1 * | 8/2016 | .......... C08F 214/282 |
| GB | 2459672 | 11/2009 | |
| JP | 2004-244504 | 9/2004 | |
| JP | 2006-232704 | 9/2006 | |
| JP | 2010-018674 | 1/2010 | |
| JP | 2011-040363 | 2/2011 | |
| JP | 2013-181128 | 9/2013 | |
| WO | WO 2000-024709 | 5/2000 | |
| WO | WO-2009096265 A1 * | 8/2009 | .......... C07D 303/08 |
| WO | WO 2014-023611 | 2/2014 | |
| WO | WO 2016-089617 | 6/2016 | |
| WO | WO 2016-100421 | 6/2016 | |

OTHER PUBLICATIONS

Olah, "Chemistry in Superacids. 6.$^{1a}$ Perfluoroalkanesulfonic Acid-Boron Perfluoroalkanesulfonates: New Superacid Systems for Generation of Carbocations and Catalysts for Electrophilic Transformations of Hydrocarbons", *Journal of Organic Chemistry*, Nov. 1984, vol. 49, No. 24, pp. 4591-4594.

Paul, "Chlorosulphuric Acid as a Non-aqueous Solvent: Part VI—Conductometric & Spectral Studies of Various Inorganic & Organic Acid", *Indian Journal of Chemistry*, Jan. 1977, vol. 15A, pp. 23-26.

Petrov, "A New Route to Polyfluorinated Trifluoromethanesulfonates Synthesis of Perfluoroallyl and Perfluorobenzyl Triflates", *Journal of Fluorine Chemistry*, Jul. 1995, vol. 73, No. 1, pp. 17-19.

Petrov, "Reaction of Boron Triflate with Polyfluoroolefins. Synthesis of Polyfluorinated Allyl Trifluoromethanesulfonates", *Journal of Organic Chemistry*, May 1998, vol. 63, No. 9, pp. 2988-2992.

Scheirs, J. (ed.), *Modern Fluoropolymers*, John Wiley & Sons, Chichester, England, 1997, p. 241.

Singh, Aluminium Tris (Fluorosulphate), *Polyhedron*, 1983, vol. 2, No. 11, pp. 1209-1210.

Wlassics, "Perfluoro Allyl Fluorosulfate (FAFS): A Versatile Building Block for New Fluoroallylic Compounds", *Molecules*, Aug. 2011, vol. 16, No. 8, pp. 6512-6540.

International Search Report for PCT International Application No. PCT/IB2018/053488 dated Dec. 7, 2018, 7 pages.

\* cited by examiner

METHODS OF MAKING A POLYFLUORINATED ALLYL ETHER AND COMPOUNDS RELATING TO THE METHODS

CROSS-REFERENCE TO RELATED APPLICATION

This application is a national stage filing under 35 U.S.C. 371 of PCT/IB2018/053488, filed May 17, 2018, which claims priority to U.S. Provisional Application No. 62/508,569, filed May 19, 2017, the disclosure of which is incorporated by reference in its entirety herein.

BACKGROUND

Synthesis of a variety of polyfluoroallyl ethers is reported in U.S. Pat. No. 4,349,650 (Krespan) and U.S. Pat. No. 4,273,729 (Krespan). The polyfluoroallyl ethers are made by the reaction of a polyfluorocarbonyl compound such as a polyfluoroketone or polyfluorocarboxylic acid fluoride with fluoride ion and a polyfluoroallyl chloride, polyfluoroallyl bromide, or polyfluoroallyl fluorosulfate. Most commonly, polyfluoroallyl ethers are synthesized by substitution of the fluorosulfate group in $CF_2=CF-CF_2-OSO_2F$ (perfluoroallyl fluorosulfate or PFAFS) by alkoxides.

Perfluoroallyl fluorosulfate is obtained by the reaction of hexafluoropropylene with $SO_3$ and $BF_3$. While effective in the reaction to make perfluoroallyl fluorosulfate, $BF_3$ is reported to be dangerous and difficult to handle (see, e.g., Wlassics et al. in "Perfluoro Allyl Fluorosulfate (FAFS): A Versatile Building Block for New Fluoroallylic Compounds" *Molecules* 2011, 16, 6512-6540.

SUMMARY

The present disclosure provides synthetic methods for making polyfluoroallyl ethers that do not require the use of $BF_3$ and synthetic intermediates associated with these methods. By comparison to $BF_3$, $BCl_3$ is much easier to handle, less toxic, less corrosive, and less expensive.

In one aspect, the present disclosure provides a method of making a compound having at least one perfluorinated allyl ether group. The method includes combining first components including at least one of $CF_2=CF-CF_2-OSO_2Cl$ or $CF_2=CF-CF_2-OSO_2CF_3$, a polyfluorinated compound comprising at least one ketone or carboxylic acid halide, and fluoride ion.

In another aspect, the present disclosure provides a method of making $CF_2=CF-CF_2-OSO_2Cl$. The method includes combining second components including $B(OSO_2Cl)_3$ and hexafluoropropylene to provide $CF_2=CF-CF_2-OSO_2Cl$.

In another aspect, the present disclosure provides a compound represented by formula $CF_2=CF-CF_2-OSO_2Cl$.

In another aspect, the present disclosure provides a method of making $CF_2=CF-CF_2-OSO_2CF_3$, the method comprising combining second components comprising $M(OSO_2CF_3)_3$ and hexafluoropropylene at a temperature greater than 0° C. to provide $CF_2=CF-CF_2-OSO_2CF_3$, wherein M is Al or B.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

"Alkyl group" and the prefix "alk-" are inclusive of both straight chain and branched chain groups and of cyclic groups. Unless otherwise specified, alkyl groups herein have up to 20 carbon atoms. Cyclic groups can be monocyclic or polycyclic and, in some embodiments, have from 3 to 10 ring carbon atoms.

The terms "aryl" and "arylene" as used herein include carbocyclic aromatic rings or ring systems, for example, having 1, 2, or 3 rings and optionally containing at least one heteroatom (e.g., O, S, or N) in the ring optionally substituted by up to five substituents including one or more alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Alkylene" is the multivalent (e.g., divalent or trivalent) form of the "alkyl" groups defined above. "Arylene" is the multivalent (e.g., divalent or trivalent) form of the "arll" groups defined above.

"Arylalkylene" refers to an "alkylene" moiety to which an aryl group is attached. "Alkylarylene" refers to an "arylene" moiety to which an alkyl group is attached.

The terms "perfluoro" and "perfluorinated" refer to groups in which all C—H bonds are replaced by C—F bonds.

The phrase "interrupted by at least one —O— group", for example, with regard to a perfluoroalkyl or perfluoroalkylene group refers to having part of the perfluoroalkyl or perfluoroalkylene on both sides of the —O— group. For example, $-CF_2CF_2-O-CF_2-CF_2-$ is a perfluoroalkylene group interrupted by an —O—.

All numerical ranges are inclusive of their endpoints and nonintegral values between the endpoints unless otherwise stated (e.g., 1 to 5 includes 1, 1.5, 2, 2.75, 3, 3.80, 4, 5, etc.).

DETAILED DESCRIPTION

The present disclosure provides a method of making a compound comprising at least one perfluorinated allyl ether group. The compound can have two or more perfluorinated ether groups. The method includes combining first components comprising at least one of $CF_2=CF-CF_2-OSO_2Cl$ or $CF_2=CF-CF_2-OSO_2CF_3$, a polyfluorinated compound comprising at least one ketone or carboxylic acid halide or combination thereof, and fluoride ion.

In some embodiments, the first components comprise $CF_2=CF-CF_2-OSO_2Cl$. $CF_2=CF-CF_2-OSO_2Cl$ can conveniently be prepared by reaction of boron trichloride ($BCl_3$) and $ClSO_3H$ to provide $B(OSO_2Cl)_3$ and subsequently reacting the $B(OSO_2Cl)_3$ and hexafluoropropylene (HFP). Accordingly, in some embodiments, the method according to the present disclosure comprises combining second components comprising $B(OSO_2Cl)_3$ and hexafluoropropylene to provide $CF_2=CF-CF_2-OSO_2Cl$, and in some embodiments, the method further comprises combining third components comprising $BCl_3$ and $ClSO_3H$ to provide $B(OSO_2Cl)_3$. The reaction of $BCl_3$ and $ClSO_3H$ can be carried out, for example, by dropwise addition of neat $ClSO_3H$ to gaseous $BCl_3$ at below 50° C. or, in the case of condensed $BCl_3$ at sub-ambient temperature. The reaction can be carried out at a temperature of least −20° C., −10° C., 0° C., 10° C., or 20° C. and up to 30° C., 40° C., or 50° C. The addition of $ClSO_3H$ to $BCl_3$ can be carried out at a rate, for example, to maintain the temperature of the mixture at 10° C. or below. $B(OSO_2Cl)_3$ can be isolated as a white powder after volatile starting materials are removed under vacuum. $B(OSO_2Cl)_3$ can then be suspended or dissolved in a solvent, and HFP can be added at below 50° C., in some embodiments, at sub-ambient temperature. For example, the reaction can be carried out at a temperature of least −20° C., −10° C., 0° C., 10° C., or 20° C. and up to 30° C., 40° C., or 50° C. Suitable solvents include halogenated solvents (e.g., methylene chloride or Freon-113). In some embodiments, the solvent is a non-aromatic solvent. $CF_2=CF—CF_2—OSO_2Cl$ can be isolated and optionally purified using conventional methods.

In some embodiments, the first components comprise $CF_2=CF—CF_2—OSO_2CF_3$. In some embodiments, the method according to the present disclosure comprises combining second components comprising $M(OSO_2CF_3)_3$ and hexafluoropropylene (HFP) to provide $CF_2=CF—CF_2—OSO_2CF_3$, wherein M is Al or B. $Al(OSO_2CF_3)_3$ is commercially available, for example, from chemical suppliers such as abcr GmbH (Karlsruhe, Germany) and Sigma-Aldrich (St. Louis, Mo.). In some embodiments, the method according to the present disclosure further comprises combining third components comprising $BCl_3$ and $CF_3SO_3H$ to provide $B(OSO_2CF_3)_3$. The reaction of $BCl_3$ and $CF_3SO_3H$ can be carried out, for example, by dropwise addition of neat $CF_3SO_3H$ to gaseous $BCl_3$ at below 50° C. or, in the case of condensed $BCl_3$ at sub-ambient temperature. The reaction can be carried out at a temperature of least −20° C., −10° C., 0° C., 10° C., or 20° C. and up to 30° C., 40° C., or 50° C. The addition of $CF_3SO_3H$ to $BCl_3$ can be carried out at a rate, for example, to maintain the temperature of the mixture at 10° C. or below. $B(OSO_2CF_3)_3$ can be isolated as a white powder after volatile starting materials are removed under vacuum.

The reaction of $M(OSO_2CF_3)_m$ and HFP is carried out neat or in presence of solvents at a temperature above 0° C. In some embodiments, the reaction is carried out at a temperature of at least 1° C., 2° C., 10° C., 20° C., 23° C., or 25° C. and up to 30° C., 40° C., 50° C., 60° C., 70° C., 0.80° C., or up to 90° C. Examples of suitable solvents include halogenated solvents (e.g., methylene chloride, 1,2-dichloroethane, or Freon-113). The reaction can be carried out for a time, for example, of at least four hours up to 40 hours.

The present disclosure provides a method of making $CF_2=CF—CF_2—OSO_2CF_3$ in which $B(OSO_2CF_3)_3$ is combined with HFP at a temperature above 0° C. In some embodiments, the reaction can be carried out at a temperature up to 50° C., 40° C., 30° C., 20° C., or 10° C. The reaction can be carried out at a temperature in a range from above 0° C. to 10° C., in some embodiments, in a range from 2° C. to 10° C., and in some embodiments, in a range from 4° C. to 8° C. The reaction mixture is combined with water at a temperature below 28° C., in some embodiments, in a range from above 25° C. to 27° C. The reaction product can then be isolated and optionally purified using conventional methods (e.g., separation of the organic fraction, drying over a drying agent, filtering, and distilling). The product $CF_2=CF—CF_2—OSO_2CF_3$ can be isolated in 75% yield, which is an improvement over the yield reported in Petrov, V. A., *J. Fluorine Chem.* 1995, 73, 17-19.

The present disclosure provides a method of making $CF_2=CF—CF_2—OSO_2CF_3$ in which $Al(OSO_2CF_3)_3$ is combined with HFP at a temperature above 0° C. In some embodiments, the reaction can be carried out at a temperature of at least 30° C., 40° C., or 50° C. and up to 90° C., 85° C., or 80° C. Conveniently, the reaction can be carried out in a steel autoclave in a suitable solvent (e.g., methylene chloride, 1,2-dichloroethane, or Freon-113) for up to 40 hours, 30 hours, or 24 hours.

Compounds represented by formula $Ti(Hal)_x(OSO_2CF_3)_y$, in which x and y are integers or non-integers, and the sum of x and y is 4, may also be useful for providing $CF_2=CF—CF_2—OSO_2CF_3$ by reaction with HFP. Compounds represented by formula $Ti(Hal)_x(OSO_2CF_3)_y$ can be made by the methods described in Mistiy, F. *J. Fluorine Chem.* 1994, 68, p. 242.

In the method of making a compound comprising at least one perfluorinated allyl ether group, first components comprising at least one of $CF_2=CF—CF_2—OSO_2Cl$ or $CF_2=CF—CF_2—OSO_2CF_3$, a polyfluorinated compound comprising at least one ketone or carboxylic acid halide, and fluoride ion are combined. The fluoride ion can be provided by a fluoride salt. In some embodiments, the source of the fluoride ion is at least one of sodium fluoride, potassium fluoride, rubidium fluoride, cesium fluoride, or $(R)_4NF$, wherein is each R is independently alkyl having from 1 to 6 carbon atoms, in some embodiments, 1 to 4 or 2 to 4 carbon atoms. Accordingly, in some embodiments, the first components comprise at least one of $CF_2=CF—CF_2—OSO_2Cl$ or $CF_2=CF—CF_2—OSO_2CF_3$, a polyfluorinated compound comprising at least one ketone or carboxylic acid halide, and at least one of sodium fluoride, potassium fluoride, rubidium fluoride, cesium fluoride, or $(R)_4NF$, wherein is each R is independently alkyl having from 1 to 6 carbon atoms. The compound of formula $(R)_4NF$ can be tetraethylammonium fluoride or tetrabutylammonium fluoride. In some embodiments, the first components comprise at least one of $CF_2=CF—CF_2—OSO_2Cl$ or $CF_2=CF—CF_2—OSO_2CF_3$, a polyfluorinated compound comprising at least one ketone or carboxylic acid halide, and at least one of sodium fluoride or potassium fluoride. In some embodiments, the fluoride ion is comprised in potassium fluoride.

In the method of making a compound comprising at least one perfluorinated allyl ether group, first components comprising at least one of $CF_2=CF—CF_2—OSO_2Cl$ or $CF_2=CF—CF_2—OSO_2CF_3$, a polyfluorinated compound comprising at least one ketone or carboxylic acid halide, and fluoride ion are combined. In some embodiments, the polyfluorinated compound comprises at least one ketone. Suitable ketones include $O=CR^3R^3$, wherein each $R^3$ is independently a linear or branched perfluoroalkyl group having from 1 to 12 carbon atoms that is optionally terminated by —$SO_2F$, —$OCF_2CF=CF_2$, —COF, —$CF(CF_3)_2$—$CF_2CO_2H$, —F, —Cl, —Br, —I, —CN, or —$CO_2$-alkyl, and optionally interrupted by one or more —O— groups. In some embodiments, the polyfluorinated compound comprising at least one ketone is hexafluoroacetone ($O=C(CF_3)_2$). Examples of other suitable polyfluorinated compounds comprising at least one ketone include chloropentafluoroacetone, 1,3-dichlorotetrafluoroacetone, 1,1-difluoroethyl-2-oxopentafluoropropanesulfonate, dimethyltetrafluoroacetone-1,3-dicarboxylate, 1,3-bis(2-heptafluoropropoxy)tetrafluoropropanone, octafluorobutanone, decafluoro-2-pentanone, dodecafluoro-2-hexanone, tetradecafluoro-2-heptanone, hexadecafluoro-2-octanone, octadecafluoro-2-nonanone, eicosafluoro-2-decanone, and 3-ketotetrafluoroglutaroyl fluoride.

In some embodiments, the polyfluorinated compound comprises at least one carboxylic acid halide. The carboxylic acid halide may be a carboxylic acid chloride or a carboxylic acid fluoride. In embodiments, the polyfluorinated compound comprises at least one carboxylic acid fluoride. Suitable carboxylic acid fluorides include $FC(O)(R^1)$ and $FC(O)(R^2)$, wherein $R^1$ is a linear or branched perfluoroalkyl group having from 2 to 12 carbon atoms that is optionally terminated by —$SO_2F$, —$OCF_2CF=CF_2$, —COF, —Cl, —Br, —I, or —$CO_2$-alkyl, and wherein $R^2$ is a linear or branched perfluoroalkyl group having from 2 to 14 carbon atoms that is interrupted by one or more ether (i.e., —O—) groups and optionally terminated by —$SO_2F$, —$OCF_2CF=CF_2$, —COF, —Cl, —Br, —I, or —$CO_2$-alkyl. Examples of suitable perfluorinated acid fluorides include trifluoroacetyl fluoride, pentafluoropropionyl fluoride, heptafluorobutyroyl fluoride, nonafluoropentanoyl fluoride, tetrafluorodiglycolyl difluoride, undecafluorohexanoyl fluoride, tridecafluoroheptanoyl fluoride, pentadecafluorooctanoyl fluoride, heptadecafluorononanoyl fluoride, nonadecafluorodecanoyl fluoride, difluoromalonyl difluoride, tetrafluorosuccinyl difluoride, hexafluoropropane-1,3-dioyl difluoride (hexafluoroglutaryl difluoride), octafluorobutane-1,4-dioyl difluoride (octafluoroadipoyl difluoride), decafluoropentane-1,5-dioyl difluoride (decafluoropimelyl difluoride), dodecafluorohexane-1,6-dioyl difluoride (dodecafluorosuberyl difluoride), fluorosulfonyldifluoroacetyl fluoride, 2-(fluorosulfonyl)-tetrafluoropropionyl fluoride, 2-(1-heptafluoropropoxy)-tetrafluoropropionyl fluoride, 2-[2-(1-heptafluoropropoxy)hexafluoropropoxy]tetrafluoropropionyl fluoride, 2-{2-[2-(1-heptafluoropropoxy)hexafluoropropoxy]hexafluoropropoxy}-tetrafluoropropionyl fluoride, carbomethoxydifluoroacetyl fluoride, cyanodifluoroacetyl fluoride, 5-carbomethoxyperfluoro(2-methyl-3-oxavaleroyl)-fluoride and 2-(pentafluorophenoxy)tetrafluoropropionyl fluoride. Further examples of suitable perfluorinated acid fluorides represented by formula $FC(O)(R^2)$ include $FC(O)CF_2OCF_3$, $FC(O)CF_2CF_2OCF_3$, $FC(O)CF_2CF_2CF_2OCF_3$, $FC(O)CF_2OCF_2CF_3$, $FC(O)CF_2CF_2OCF_2CF_3$, $FC(O)CF_2CF_2CF_2OCF_2CF_3$, $FC(O)CF_2OCF_2CF_2OCF_3$, $FC(O)CF_2OCF_2CF_2CF_2OCF_3$, $FC(O)CF_2OCF_2CF_2CF_2CF_2OCF_3$, $FC(O)CF_2OCF_2CF_2CF_3$, $FC(O)CF_2OCF_2OCF_2CF_2CF_3$, $FC(O)CF(CF_3)$—O—$C_3F_7$, and $FCOCF(CF_3)OCF_2CF(CF_3)$—O—$C_3F_7$.

Many of the polyfluorinated compounds having at least one ketone or carboxylic acid halide are commercially available. Others can be prepared by known methods. See, for example, U.S. Pat. No. 4,273,729 (Krespan) and the references cited therein.

In general, to provide a monofunctional perfluorinated allyl ether, the molar equivalents of the first components (that is, at least one of $CF_2=CF$—$CF_2$—$OSO_2Cl$ or $CF_2=CF$—$CF_2$—$OSO_2CF_3$, a polyfluorinated compound comprising at least one ketone or carboxylic acid halide, and fluoride ion) are substantially the same. The term "substantially" with regard to the molar equivalents of the first components means that the molar amount of any one of the $CF_2=CF$—$CF_2$—$OSO_2Cl$ or $CF_2=CF$—$CF_2$—$OSO_2CF_3$, a polyfluorinated compound comprising at least one ketone or carboxylic acid halide, or fluoride ion may exceed any other one of these components by up to 10 mol %, 7.5 mol %, or 5 mol %.

In some embodiments, a polyfluorinated compound comprising at least one ketone or carboxylic acid halide and a fluoride salt (including any of those described above in any of their embodiments) are first combined to provide an alkoxide, which is then combined with at least one of $CF_2=CF$—$CF_2$—$OSO_2Cl$ or $CF_2=CF$—$CF_2$—$OSO_2CF_3$ without isolation of the alkoxide. The alkoxide can be prepared in a suitable solvent. Suitable solvents include polar, aprotic solvents, for example, N,N-dimethylformamide (DMF), acetonitrile, N,N-dimethylacetamide (DMAC), gamma-butyrolactone, 1,2-dimethoxyethane (glyme), 1-(2-methoxyethoxy)-2-methoxyethane (diglyme), 2,5,8,11-tetraoxadodecane (triglyme), dioxane, sulfolane, nitrobenzene, and benzonitrile. Conveniently, the $CF_2=CF$—$CF_2$—$OSO_2Cl$, $CF_2=CF$—$CF_2$—$OSO_2CF_3$, or combination thereof is added to the alkoxide in any one of these solvents. In some embodiments, the solvent is diglyme. The formation of the alkoxide can conveniently be carried out under an inert atmosphere at sub-ambient temperatures, in some embodiments, in a range from 0° C. to 10° C. During and after the addition of at least one of $CF_2=CF$—$CF_2$—$OSO_2Cl$ or $CF_2=CF$—$CF_2$—$OSO_2CF_3$, the reaction mixture can be stirred below room temperature, in some embodiments, in a range from 0° C. to 15° C., and allowed to warm to room temperature, in some embodiments, in a range from 25° C. to 30° C.

In some embodiments of the method according to the present disclosure, the compound comprising at least one perfluorinated allyl ether group is represented by formula $CF_2=CFCF_2(OC_nF_{2n})_zORf$, wherein each n is independently from 2 to 6, z is 0, 1, or 2, and Rf is a linear or branched perfluoroalkyl group having from 1 to 8 carbon atoms and optionally interrupted by one or more —O— groups. In some embodiments, z is 0, and Rf is a linear or branched alkyl group having from 1 to 6 or 1 to 4 carbon atoms. Specific examples of these Rf groups include $C_2F_5$, $C_3F_7$, and $C_4F_9$. In some embodiments, $C_3F_7$ and $C_4F_9$ are linear.

In some embodiments of formula $CF_2=CFCF_2(OC_nF_{2n})_zORf$, z is 1 or 2, n is 2 to 3, and Rf is a linear or branched alkyl group having from 1 to 6 or 1 to 4 carbon atoms. Examples of such perfluoroalkoxyalkyl allyl ethers include
$CF_2=CFCF_2OCF_2CF_2OCF_3$,
$CF_2=CFCF_2OCF_2CF_2CF_2OCF_3$,
$CF_2=CFCF_2OCF_2CF_2CF_2CF_2OCF_3$,
$CF_2=CFCF_2OCF_2CF_2OCF_2CF_3$,
$CF_2=CFCF_2OCF_2CF_2CF_2OCF_2CF_3$,
$CF_2=CFCF_2OCF_2CF_2CF_2CF_2OCF_2CF_3$,
$CF_2=CFCF_2OCF_2CF_2OCF_2OCF_3$,
$CF_2=CFCF_2OCF_2OCF_2CF_2OCF_3$,
$CF_2=CFCF_2OCF_2OCF_2CF_2CF_2OCF_3$,
$CF_2=CFCF_2OCF_2OCF_2CF_2CF_2CF_2OCF_3$,
$CF_2=CFCF_2OCF_2CF_2CF_2CF_2CF_2OCF_3$,
$CF_2=CFCF_2OCF_2CF_2OCF_2CF_3$,
$CF_2=CFCF_2OCF_2CF_2OCF_2OCF_2CF_3$,
$CF_2=CFCF_2OCF_2CF(CF_3)$—O—$C_3F_7$, and $CF_2=CFCF_2(OCF_2CF(CF_3))_2$—O—$C_3F_7$.

In some embodiments of the method according to the present disclosure, the compound comprising at least one perfluorinated allyl ether group is represented by formula $CF_2=CF$—$CF_2$—O—$R_F$—O—$CF_2$—$CF=CF_2$, wherein RF represents linear or branched perfluoroalkylene or perfluoropolyoxyalkylene or arylene, which may be non-fluorinated or fluorinated. In some embodiments, $R_F$ is perfluoroalkylene having from 1 to 12, from 2 to 10, or from 3 to 8 carbon atoms. The arylene may have from 5 to 14, 5 to 12, or 5 to 10 carbon atoms and may be non-substituted or substituted with one or more halogens other than fluoro, perfluoroalkyl (e.g. —$CF_3$ and —$CF_2CF_3$), perfluoroalkoxy (e.g. —O—$CF_3$, —$OCF_2CF_3$), perfluoropolyoxyalkyl (e.g., —$OCF_2OCF_3$; —$CF_2OCF_2OCF_3$), fluorinated, perfluorinated, or non-fluorinated phenyl or phenoxy, which may be substituted with one or more perfluoroalkyl, perfluoroalkoxy, perfluoropolyoxyalkyl groups, one or more halogens other than fluoro, or combinations thereof. In some embodiments, RF is phenylene or mono-, di-, tri- or tetrafluorophenylene, with the ether groups linked in the ortho, para or meta position. In some embodiments, $R_F$ is $(CF_2)_q$ wherein q is 2, 3, 4, 5, 6, 7 or 8; $CF_2$—O—$CF_2$—$CF_2$; $CF(CF_3)$; $(CF_2)_2$—O—$CF(CF_3)$—$CF_2$; $CF(CF_3)$—$CF_2$—O—$CF(CF_3)$; or $(CF_2)_2$—O—$CF(CF_3)$—$CF_2$—O—$CF(CF_3)$—$CF_2$—O—$CF_2$. In some embodiments, $R_F$ is $CF_2$—$CF_2$—$CF_2$—$CF_2$. Such compounds represented by formula $CF_2$=CF—$CF_2$—O—$R_F$—O—$CF_2$—CF=$CF_2$ can introduce long chain branches as described in U.S. Pat. Appl. Pub. No. 2010/0311906 (Lavallée et al.).

In general, to prepare a compound represented by formula $CF_2$=CF—$CF_2$—O—$R_F$—O—$CF_2$—CF=$CF_2$, two molar equivalents of $CF_2$=CF—$CF_2$—$OSO_2Cl$, $CF_2$=CF—$CF_2$—$OSO_2CF_3$, or a combination thereof and two molar equivalents of fluoride ion may be used. The molar equivalents of $CF_2$=CF—$CF_2$—$OSO_2Cl$, $CF_2$=CF—$CF_2$—$OSO_2CF_3$, and fluoride ion may deviate from two molar equivalents by up to 10 mol %, 7.5 mol %, or 5 mol %.

Compounds comprising at least one perfluorinated allyl ether group made according to the methods of the present disclosure are useful, for example, in the preparation of fluoropolymers. For example, compounds comprising at least one perfluorinated allyl ether group can be interpolymerized with at least one partially fluorinated or perfluorinated ethylenically unsaturated monomer represented by formula $R^aCF$=$CR^a{}_2$, wherein each W is independently fluoro, chloro, bromo, hydrogen, a fluoroalkyl group (e.g. perfluoroalkyl having from 1 to 8, 1 to 4, or 1 to 3 carbon atoms and optionally interrupted by one or more oxygen atoms), alkyl having up to 10 carbon atoms, alkoxy having up to 8 carbon atoms, or aryl having up to 8 carbon atoms. Examples of useful fluorinated monomers represented by formula $R^aCF$=$CR^a{}_2$ include vinylidene fluoride (VDF), tetrafluoroethylene (TFE), hexafluoropropylene (HFP), chlorotrifluoroethylene, 2-chloropentafluoropropene, trifluoroethylene, vinyl fluoride, dichlorodifluoroethylene, 1,1-dichlorofluoroethylene, 1-hydropentafluoropropylene, 2-hydropentafluoropropylene, tetrafluoropropylene, and mixtures thereof. Compounds comprising at least one perfluorinated allyl ether group can be useful for preparing amorphous fluoropolymers, semi-crystalline thermoplastics, and non-melt processable fluoroplastics.

In some embodiments, one or more compounds comprising at least one perfluorinated allyl ether group can be copolymerized with TFE to form a non-melt processable fluoroplastic. The fluorinated allyl ether may be any of those described above. In a non-melt processable fluoroplastic, one or more compounds comprising at least one perfluorinated allyl ether group are included in the monomers for polymerization in an amount of up to about one percent by weight. TFE homo- and copolymers including a comonomer in an amount of up to about one percent by weight are referred to in the art as PTFE. PTFE has such a high melt viscosity and/or low melt flow index (WFI) that it cannot be processed by conventional melt processing techniques such as extrusion, injection molding, or blow molding. In some embodiments, the fluoropolymer contains TFE units and units from at least one perfluoroalkyl allyl ether comonomer and no other comonomer units. The amount of the perfluorinated allyl ether comonomer units may be up to 1% by weight or up to 0.1% by weight. For example, the amount of the perfluorinated allyl ether comonomer units can be from 0.1 to 1 percent by weight or from 0.3 to 1 percent by weight, based on the total weight of the fluoropolymer (in which the comonomer units add up to give 100% by weight).

The molecular weights of certain fluoroplastics are often characterized by the melt viscosity or the melt flow index (MFI; e.g., 372° C./5 kg). In some embodiments, the non-melt-processable fluoropolymer made from the compound comprising at least one perfluorinated allyl ether group has a melt flow index (WTI) of 1.0 g/10 min or less at 372° C. using a 5 kg load (WTI 372/5 of less than 1.0 g/10 min), in some embodiments, a melt flow index (372/5) of 0.1 g/10 minutes or less. In some embodiments, the non-melt-processable fluoropolymer has a melting point of at least 300° C., in some embodiments, at least 315° C., and typically within the range of 327+/−10° C. In some embodiments, the non-melt-processable fluoropolymer has a melting point of at least 317° C., at least 319° C., or at least 321° C. The melting point of not melt-processable fluoropolymers differs when the material is molten for the first time and after subsequent melting. After the material has been molten once, the meting point in subsequent melting remains constant. The melting point as referred to herein is the melting point of previously molten material (i.e., the material was brought to the melting point, cooled below its melting point, and then melted again).

PTFEs made with one or more compounds comprising at least one perfluorinated allyl ether group made by the methods disclosed herein can be useful, for example, for gaskets and inner liners for pipes and containers.

In some embodiments, one or more compounds comprising at least one perfluorinated allyl ether group can be copolymerized with TFE to form a fluorothermoplastic. Copolymers of TFE and perfluorinated allyl ethers are known in the art as PFA's (perfluorinated alkoxy polymers). In these embodiments, the fluorinated allyl ether units are present in the copolymer in an amount in a range from 0.01 mol % to 15 mol %, in some embodiments, 0.05 mol % to 10 mol %, and in some embodiments, 0.5 mol % to 5 mol %. The fluorinated allyl ether may be any of those described above. In some embodiments, the fluorinated allyl ether comprises at least one of perfluoro (methyl allyl) ether, perfluoro (ethyl allyl) ether, perfluoro (n-propyl allyl) ether. In some embodiments, the copolymer of TFE and at least one perfluorinated allyl ether consists essentially of units derived from TFE and at least one compound comprising at least one perfluorinated allyl ether. "Consisting essentially of" as used herein refers to the absence of other comonomers or the presence of units derived from other comonomers in an amount of less than one percent by weight, in some embodiments, less than 0.1 percent by weight. In some embodiments, the copolymer of TFE and at least one perfluorinated allyl ether further comprises at least one percent by weight, up to 10, 6, 5, or 4 percent by weight of other units derived from compounds represented by formula $R^aCF$=$CR^a{}_2$ described above, non-fluorinated olefins (e.g., ethene or propene), and/or bis(allyl ethers) described above. In some embodiments, at least one of HFP, VDF, vinyl fluoride, chlorotrifluoroethylene, ethene, or propene is included in the monomers to make the PFA copolymer. In some embodiments, the fluorothermoplastic made from the compound comprising at least one perfluorinated allyl ether group has a melt flow index (MFI) in a range from 0.5 g/10 min to 100 g/10 min at 372° C. using a 5 kg load (MFI 372/5 of in a range from 0.5 g/10 min to 100 g/10 min). In some embodiments, the copolymer has a melting point of from 270° C. to 326° C. and a melt flow index (MFI at 372° C. and 5 kg load) of 0.5 to 19 grams/10 minutes. In some embodiments, the copolymer has a melting point of from 250° C. to 290° C. and have a melt flow index (MFI at 372° C. and 5 kg load) of from 31 grams/10 minutes to 50 grams/10 minutes.

In some embodiments, one or more compounds comprising at least one perfluorinated allyl ether group can be copolymerized with TFE and HFP. The fluorinated allyl ether may be any of those described above. Copolymers of TFE and HFP with or without other perfluorinated comonomers are known in the art as FEP's (fluorinated ethylene propylene). In some embodiments, these fluorothermoplastics are derived from copolymerizing 30 to 70 wt. % TFE, 10 to 30 wt. %, HFP, and 0.2 to 50 wt. % of one or more of the compounds comprising at least one perfluorinated allyl ether group. These weight percentages are based on the weight of the polymer, and the comonomers add up to give 100% by weight. In some embodiments, units derived from the compound(s) comprising at least one perfluorinated allyl ether are present in the copolymer according to the present disclosure in a range from 0.2 percent by weight to 12 percent by weight, based on the total weight of the copolymer. In some embodiments, units derived from the perfluorinated allyl ether are present in a range from 0.5 percent by weight to 6 percent by weight, based on the total weight of the copolymer, with the total weight of the copolymer being 100% by weight. In some embodiments, units derived from the compound(s) comprising at least one perfluorinated allyl ether are present in the copolymer according to the present disclosure in a range from 0.02 mole percent to 2 mole percent, based on the total amount of the copolymer. In some embodiments, units derived from the perfluorinated allyl ether are present in the copolymer in an amount up to 1.5 mole percent or up to 1.0 mole percent. In some embodiments, the copolymerized units represented by this formula are present in the copolymer in an amount of at least 0.03 mole percent or 0.05 mole percent. The copolymerized units may be present in the copolymer in a range from 0.02 mole percent to 2 mole percent, 0.03 mole percent to 1.5 mole percent, or 0.05 mole percent to 1.0 mole percent. Copolymers made according to the methods of the present disclosure may be made from any combination of one or more compounds comprising at least one allyl ether group according to any of the above embodiments. The HFP may be present in a range from 5 wt. % to 22 wt. %, in a range from 10 wt. % to 17 wt. %, in a range from 11 wt. % to 16 wt. %, or in a range from 11.5 wt. % to 15.8 wt. %, based on the total weight of the copolymer, wherein the weight of the copolymer is 100% by weight. The copolymers made according to the methods of the present disclosure typically have a melting point between 220° C. to 285° C., in some embodiments, 235° C. to 275° C., 240° C. to 275° C., or 245° C. to 265° C. In some embodiments, the copolymer prepared from the compound(s) comprising at least one perfluorinated allyl ether group, TFE, and HFP has an MFI at 372° C. and 5 kg load of 30±10 grams per 10 minutes. In some embodiments, the copolymer prepared from the compound(s) comprising at least one perfluorinated allyl ether group, TFE, and HFP has an MFI at 372° C. and 5 kg load of 30±5 grams per 10 minutes or 30±3 grams per 10 minutes. In some embodiments, the copolymer prepared from the compound(s) comprising at least one perfluorinated allyl ether group, TFE, and HFP has an MFI at 372° C. and 5 kg load in a range from 1 gram per 10 minutes to 19 grams per 10 minutes. In some embodiments, this copolymer has an MFI in a range from 1 gram per 10 minutes to 15 grams per 10 minutes or in a range from 1 gram per 10 minutes to 10 grams per 10 minutes.

FEPs made with one or more compounds comprising at least one perfluorinated allyl ether group made by the methods disclosed herein can be useful, for example, for electrical insulation in Local Area Networks (LAN).

In some embodiments, one or more compounds comprising at least one perfluorinated allyl ether group made by the methods disclosed herein can be used to make amorphous fluoropolymers. Amorphous fluoropolymers typically do not exhibit a melting point and exhibit little or no crystallinity at room temperature. Useful amorphous fluoropolymers can have glass transition temperatures below room temperature or up to 280° C. Suitable amorphous fluoropolymers can have glass transition temperatures in a range from −60° C. up to 280° C., −60° C. up to 250° C., from −60° C. to 150° C., from −40° C. to 150° C., from −40° C. to 100° C., or from −40° C. to 20° C.

In some embodiments, polymerized units derived from the one or more compounds comprising at least one perfluorinated allyl ether group are present in the amorphous fluoropolymer at up to 50 mole percent of the fluoropolymer, in some embodiments up to 30 mole percent or up to 10 mole percent. The fluorinated allyl ether may be any of those described above.

In some embodiments, amorphous fluoropolymers that can be prepared using the methods disclosed herein include a TFE/perfluoromethyl allyl ether copolymer, a TFE/$CF_2$=$CFCF_2OC_3F_7$ copolymer, a TFE/$CF_2$=$CFCF_2OCF_3$/$CF_2$=$CFCF_2OC_3F_7$ copolymer, a VDF/$CF_2$=$CFCF_2OC_3F_7$ copolymer, a TFE/VDF/perfluoromethyl allyl ether/ethylene copolymer, or a TFE/VDF/$CF_2$=$CFCF_2O(CF_2)_3OCF_3$ copolymer.

In some embodiments, the amorphous fluoropolymer that can be prepared using the methods of the present disclosure includes polymerized units comprising a cure site. In these embodiments, cure site monomers may be useful during the polymerization to make the amorphous fluoropolymer. Such cure site monomers include those monomers capable of free radical polymerization. The cure site monomer can be perfluorinated to ensure adequate thermal stability of the resulting elastomer. Examples of useful cure sites include a Br cure site, an I cure site, a nitrile cure site, a carbon-carbon double bond, and combinations thereof. Any of these cure sites can be cured using peroxides, for example. However, in some cases in which multiple, different cure sites are present a dual cure system or a multi cure system may be useful. Other suitable cure systems that may be useful include bisphenol curing systems or triazine curing systems. Useful amounts of the cure site monomers include 0.01 mol % to 1 mol %, based on total moles of monomer incorporated into the polymer may be used. In some embodiments, at least 0.02, 0.05, or even 0.1 mol % of a cure site monomer is used and at most 0.5, 0.75, or even 0.9 mol % of a cure site monomer is used based on the total moles of monomer incorporated into the amorphous fluoropolymer.

In some embodiments, the cure site monomer can comprise at least one of $CF_2$=CF—$CF_2$—O—$CF_2$—$CF_2$—$CF_2I$, $CF_2$=CF—$CF_2$—O—$CF_2$—$CF_2$—$CF_2Br$, $CF_2$=CF—$CF_2$—O—$CF_2$—$CF_2$—I, $CF_2$=CF—$CF_2$—O—$CF_2$—$CF_2Br$, $CF_2$=CF—$CF_2$—O—$(CF_2)_2$—O—$C_2F_4I$, $CF_2$=CF—$CF_2$—O—$(CF_2)_3$—O—$C_2F_4I$, $CF_2$=CF—$CF_2$—O—$(CF_2)_4$—O—$C_2F_4I$, $CF_2$=CF—$CF_2$—O—$(CF_2)_5$—O—$C_2F_4I$, $CF_2$=CF—$CF_2$—O—$(CF_2)_6$—O—$C_2F_4I$, $CF_2$=CF—$CF_2$—O—$C_4F_8I$, $CF_2$=CF—$CF_2$—O—$CF_2CF(CF_3)$—O—$C_2F_4I$, $CF_2$=CF—$CF_2$—(OCF_2CF(CF_3))_2$—O—$C_2F_4I$, $CF_2$=CF—$CF_2$—O—$CF_2CFI$—$CF_3$, or $CF_2$=CF—$CF_2$—O—$CF_2CF(CF_3)$—O—$CF_2CFI$—$CF_3$. Such cure site monomers may be made by the method according to the present disclosure, for example, with a polyfluorinated compound comprising a carboxylic acid fluoride and a bromo or iodo substituent. Such polyfluorinated acid fluorides include $FC(O)-CF_2-CF_2I$, $FC(O)-CF_2-CF_2Br$, $FC(O)-CF_2-I$, $FC(O)-CF_2-Br$, $FC(O)-CF_2-O-C_2F_4I$, $FC(O)-(CF_2)_2-O-C_2F_4I$, $FC(O)-(CF_2)_3-O-C_2F_4I$, $FC(O)-(CF_2)_4-O-C_2F_4I$, $FC(O)-(CF_2)_5-O-C_2F_4I$, $FC(O)-C_3F_6I$, $FC(O)-CF(CF_3)-O-C_2F_4I$, $FC(O)-CF(CF_3)OCF_2CF(CF_3)-O-C_2F_4I$, $FC(O)-CFI-CF_3$, and $FC(O)-CF(CF_3)-O-CF_2CFI-CF_3$.

In some embodiments, the amorphous fluoropolymer that can be prepared using the methods of the present disclosure includes polymerized units comprising a nitrile cure site. Nitrile cure sites can be introduced into the polymer by using nitrile containing monomers during the polymerization. Examples of suitable nitrile containing monomers include those represented by formulas $CF_2=CF-CF_2-O-Rf-CN$, wherein Rf is a perfluoroalkylene or a bivalent perfluoroether group. Such cure site monomers may be made by the method according to the present disclosure, for example, with a polyfluorinated compound comprising a carboxylic acid fluoride and a nitrile substituent (e.g., $FC(O)Rf-CN$).

In some embodiments, the amorphous fluoropolymer that can be prepared using the methods of the present disclosure includes polymerized units comprising $CF_2=CF-CF_2-O-R_F-O-CF_2-CF=CF_2$ as a cure site monomer, wherein $R_F$ can be as described above in any of its embodiments. The compound represented by formula $CF_2=CF-CF_2-O-R_F-O-CF_2-CF=CF_2$ may be present in the components to be polymerized in any useful amount, in some embodiments, in an amount of up to 2, 1, or 0.5 mole percent and in an amount of at least 0.1 mole percent, based on the total amount of polymerizable components.

If the amorphous fluoropolymer is perhalogenated, in some embodiments perfluorinated, typically at least 50 mole percent (mol %) of its interpolymerized units are derived from TFE and/or CTFE, optionally including HFP. The balance of the interpolymerized units of the amorphous fluoropolymer (e.g., 10 to 50 mol %) is made up of one or more of the compounds comprising at least one perfluorinated allyl ether group, and, in some embodiments, a cure site monomer. If the fluoropolymer is not perfluorinated, it typically contains from about 5 mol % to about 90 mol % of its interpolymerized units derived from TFE, CTFE, and/or HFP; from about 5 mol % to about 90 mol % of its interpolymerized units derived from VDF, ethylene, and/or propylene; up to about 40 mol % of its interpolymerized units derived from one or more compounds comprising at least one perfluorinated allyl ether group; and from about 0.1 mol % to about 5 mol %, in some embodiments from about 0.3 mol % to about 2 mol %, of a cure site monomer.

In some embodiments, compounds comprising at least one perfluorinated allyl ether group that can be prepared according to the methods of the present disclosure further comprise $-SO_2X$ groups, wherein X is independently F, $-NZH$, $-NZSO_2(CF_2)_{1-6}SO_2X'$, $-NZ[SO_2(CF_2)_aSO_2NZ]_{1-10}SO_2(CF_2)_aSO_2X'$ (in which each a is independently 1 to 6, 1 to 4, or 2 to 4), or $-OZ$. In some embodiments, X is independently $-F$, $-NZH$, or $-OZ$. In some embodiments, X is $-NZH$ or $-OZ$. In some embodiments, X is $-F$. X' is independently $-NZH$ or $-OZ$ (in some embodiments, $-OZ$). In any of these embodiments, each Z is independently a hydrogen, an alkali metal cation, or a quaternary ammonium cation. The quaternary ammonium cation can be substituted with any combination of hydrogen and alkyl groups, in some embodiments, alkyl groups independently having from one to four carbon atoms. In some embodiments, Z is an alkali-metal cation. In some embodiments, Z is a sodium or lithium cation. In some embodiments, Z is a sodium cation. The compound comprising one least one allyl ether group that can be made by the method disclosed herein can be represented by formula $CF_2=CFCF_2-(OC_bF_{2b})_c-O-(C_eF_{2e})-SO_2X$. In this formula, b is a number from 2 to 8, 0 or 2, and e is a number from 1 to 8. In some embodiments, b is a number from 2 to 6 or 2 to 4. In some embodiments, b is 2. In some embodiments, e is a number from 1 to 6 or 2 to 4. In some embodiments, e is 2. In some embodiments, e is 4. In some embodiments, c is 0 or 1. In some embodiments, c is 0. In some embodiments, c is 0, and e is 2 or 4. In some embodiments, b is 3, c is 1, and e is 2. $C_eF_{2e}$ may be linear or branched. In some embodiments, $C_eF_{2e}$ can be written as $(CF_2)_e$, which refers to a linear perfluoroalkylene group. When c is 2, the b in the two $C_bF_{2b}$ groups may be independently selected. However, within a $C_bF_{2b}$ group, a person skilled in the art would understand that b is not independently selected. Examples of useful compounds represented by formula $CF_2=CFCF_2-(OC_bF_{2b})_c-O-(C_eF_{2e})-SO_2X$ include $CF_2=CFCF_2-O-CF_2-SO_2X$, $CF_2=CFCF_2-O-CF_2CF_2-SO_2X$, $CF_2=CFCF_2-O-CF_2CF_2CF_2-SO_2X$, $CF_2=CFCF_2-O-CF_2CF_2CF_2CF_2-SO_2X$, and $CF_2=CFCF_2-O-CF(CF_3)-CF_2-O-(CF_2)_e-SO_2X$.

Compounds with $-SO_2X$ groups can be prepared by the methods according to the present disclosure, for example, starting from a polyfluorinated compound comprising a ketone or carboxylic acid fluoride and a sulfonyl fluoride ($-SO_2F$) substituent. Examples of such polyfluorinated acid fluorides and ketone include $FC(O)-CF_2-SO_2F$, $FC(O)-CF_2CF_2-SO_2F$, $FC(O)-CF_2CF_2CF_2-SO_2F$, and $O=C(CF_3)-CF_2-O-(CF_2)_e-SO_2F$. After the polyfluorinated acid fluoride or carboxylic acid is combined with at least one of $CF_2=CF-CF_2-OSO_2Cl$ or $CF_2=CF-CF_2-OSO_2CF_3$ and a fluoride salt to make the compound represented by formula $CF_2=CFCF_2-(OC_bF_{2b})_c-O-(C_eF_{2e})-SO_2F$, the $-SO_2F$ groups may be hydrolyzed or treated with ammonia using conventional methods to provide $-SO_3Z$ or $-SO_2NZH$ groups. Hydrolysis of a copolymer having $-SO_2F$ groups with an alkaline hydroxide (e.g. LiOH, NaOH, or KOH) solution provides $-SO_3Z$ groups, which may be subsequently acidified to $SO_3H$ groups. Treatment of a compound having $-SO_2F$ groups with water and steam can form $SO_3H$ groups.

Sulfonamides (e.g., polyfluorinated allyl ether compounds having $-SO_2NH_2$ groups) can be further reacted with multi-functional sulfonyl fluoride or sulfonyl chloride compounds. Examples of useful multi-functional compounds include 1,1,2,2-tetrafluoroethyl-1,3-disulfonyl fluoride; 1,1,2,2,3,3-hexafluoropropyl-1,3-disulfonyl fluoride; 1,1,2,2,3,3,4,4-octafluorobutyl-1,4-disulfonyl fluoride; 1,1,2,2,3,3,4,4,5,5-perfluorobutyl-1,5-disulfonyl fluoride; 1,1,2,2-tetrafluoroethyl-1,2-disulfonyl chloride; 1,1,2,2,3,3-hexafluoropropyl-1,3-disulfonyl chloride; 1,1,2,2,3,3,4,4-octafluorobutyl-1,4-disulfonyl chloride; and 1,1,2,2,3,3,4,4,5,5-perfluorobutyl-1,5-disulfonyl chloride. After hydrolysis of the sulfonyl halide groups, a compound of formula $CF_2=CFCF_2-(OC_bF_{2b})_c-O-(C_eF_{2e})-SO_2X$, in which X is $-NZSO_2(CF_2)_{1-6}SO_3Z$, can be made. Polyfluorinated allyl ether compounds bearing $-SO_2NH_2$ groups can also be treated with polysulfonimides represented by formula $FSO_2(CF_2)_a[SO_2NZSO_2(CF_2)_a]_{1-10}SO_2F$ or $FSO_2(CF_2)_a[SO_2NZSO_2(CF_2)_a]_{1-10}SO_3H$, wherein each a is independently 1 to 6, 1 to 4, or 2 to 4. To make a polysulfonimide, a sulfonyl halide monomer (e.g., any of those described above) and a sulfonamide monomer represented by formula $H_2NSO_2(CF_2)_aSO_2NH_2$ are made to react in the mole ratio of $(k+1)/k$. The reaction may be carried out, for example, in a suitable solvent (e.g., acetonitrile) at 0° C. in the presence of base. The sulfonyl halide monomer and sulfonamide monomer may have the same or different values of a, resulting in the same or different value of a for each repeating unit. The resulting product $FSO_2(CF_2)_a[SO_2NZSO_2(CF_2)_a]_{1-10}SO_2F$ may be treated with one equivalent of water in the presence of base (e.g., N,N-diisopropylethylamine (DIPEA)) to provide $FSO_2(CF_2)_a[SO_2NZSO_2(CF_2)_a]_{1-10}SO_3H$, as described in JP 2011-40363.

Compounds represented by formula $CF_2=CFCF_2—(OC_bF_{2b})_c—O—(C_eF_{2e})—SO_2F$ can also be treated with small molecule sulfonamides such as those represented by formula $NH_2SO_2(CF_2)_{1-6}SO_3Z$, wherein Z is as defined above in any of its embodiments, to provide $—SO_2NHSO_2(CF_2)_{1-6}SO_3Z$ groups. Compounds represented by formula $NH_2SO_2(CF_2)_{1-6}SO_3Z$ may be synthesized by reacting cyclic perfluorodisulfonic acid anhydrides with amines according to the methods described in U.S. Pat. No. 4,423,197 (Behr).

Compounds represented by formula $CF_2=CFCF_2—(OC_bF_{2b})_c—O—(C_eF_{2e})—SO_2X$ as described above in any of their embodiments can be copolymerized with compounds represented by formula $R^aCF=CR^a_2$, as described above in any of their embodiments. Suitable monomers that may be included in the components to be polymerized can also include perfluoroallyl ether (e.g., perfluoroalkyl allyl ether or perfluoroalkoxyalkyl allyl ether as described above in any of their embodiments). The allyl ethers described above in any of their embodiments, may be present in the components to be polymerized in any useful amount, in some embodiments, in an amount of up to 10, 7.5, or 5 mole percent, based on the total amount of polymerizable components. Conveniently, copolymers can also be made by reaction of compounds represented by formula $CF_2=CFCF_2—(OC_bF_{2b})_c—O—(C_eF_{2e})—SO_2F$ as described above in any of their embodiments with compounds represented by formula $R^aCF=CR^a_2$, as described above in any of their embodiments. Hydrolysis and reactions to make sulfonimides and polysulfonimides can then be carried out with the polymeric sulfonyl fluorides using the methods described above.

The copolymer made from compounds represented by formula $CF_2=CFCF_2—(OC_bF_{2b})_c—O—(C_eF_{2e})—SO_2X$ and $R^aCF=CR^a_2$ are referred to as ionomers and can have $—SO_2X$ equivalent weight of up to 1000, 900, 800, 750, 700, or 600. In some embodiments, the copolymer or ionomer has an $—SO_2X$ equivalent weight of at least 400. In general, the $—SO_2X$ equivalent weight of the copolymer refers to the weight of the copolymer containing one mole of $—SO_2X$ groups, wherein X is as defined above in any of its embodiments. In some embodiments, the $—SO_2X$ equivalent weight of the copolymer refers to the weight of the copolymer that will neutralize one equivalent of base. In some embodiments, the $—SO_2X$ equivalent weight of the copolymer refers to the weight of the copolymer containing one mole of sulfonate groups (i.e., $—SO_3^-$). Decreasing the $—SO_2X$ equivalent weight of the copolymer or ionomer tends to increase electrical conductivity in the copolymer or ionomer but tends to decrease its crystallinity, which may compromise the mechanical properties of the copolymer. Thus, the $—SO_2X$ equivalent weight may be selected based on a balance of the requirements for the electrical and mechanical properties of the copolymer or ionomer. In some embodiments, the $—SO_2X$ equivalent weight of the copolymer refers to the weight of the copolymer containing one mole of sulfonamide groups (i.e., $—SO_2NH$). Sulfonimide groups (e.g., when X is $—NZSO_2(CF_2)_{1-6}SO_2X'$ and $—NZ[SO_2(CF_2)_aSO_2NZ]_{1-10}SO_2(CF_2)_aSO_2X'$) also function as acid groups that can neutralize base as described in further detail below. The effective equivalent weight of copolymers including these groups can be much lower than 1000.

In some embodiments, ionomers are prepared from components including up to 40 mole percent of at least one compound represented by formula $CF_2=CFCF_2—(OC_bF_{2b})_c—O—(C_eF_{2e})—SO_2X$, in any of their embodiments described above, based on the total amount of components. In some embodiments, the components comprise up to 35, 30, 25, or 20 mole percent of a compound represented by formula $CF_2=CFCF_2—(OC_bF_{2b})_c—O—(C_eF_{2e})—SO_2X$, based on the total amount of components. Ionomers may be useful, for example, in the manufacture of polymer electrolyte membranes for use in fuel cells or other electrolytic cells.

In embodiments in which the methods disclosed herein comprise combining the compound comprising at least one perfluorinated allyl ether group with at least one partially fluorinated or perfluorinated ethylenically unsaturated monomer represented by formula $R^aCF=CR^a_2$, the reaction can be carried out by free-radical polymerization. Conveniently, in some embodiments, the methods of making the copolymer disclosed herein includes radical aqueous emulsion polymerization.

In some embodiments of the methods of making the copolymer according to the present disclosure, a water-soluble initiator (e.g., potassium permanganate or a peroxy sulfuric acid salt) can be useful to start the polymerization process. Salts of peroxy sulfuric acid, such as ammonium persulfate or potassium persulfate, can be applied either alone or in the presence of a reducing agent, such as bisulfites or sulfinates (e.g., fluorinated sulfinates disclosed in U.S. Pat. Nos. 5,285,002 and 5,378,782, both to Grootaert) or the sodium salt of hydroxy methane sulfinic acid (sold under the trade designation "RONGALIT", BASF Chemical Company, New Jersey, USA). The choice of initiator and reducing agent, if present, will affect the end groups of the copolymer. The concentration range for the initiators and reducing agent can vary from 0.01% to 5% by weight based on the aqueous polymerization medium. When salts of peroxy sulfuric acid are used in the presence of a sulfite or bisulfite salt (e.g., sodium sulfite or potassium sulfite), $SO_3^-$× radicals are generated during the polymerization process, resulting in $—SO_3^-$ end groups. It might be useful to add metal ions to catalyze or accelerate the formation of $-SO_3^-$ radicals. By altering the stoichiometry of the sulfite or bisulfite salt versus the peroxy sulfuric acid salt, one can control the amount of $-SO_2X$ end groups.

Most of the initiators described above and any emulsifiers that may be used in the polymerization have an optimum pH-range where they show most efficiency. For this reason, buffers may be useful. Buffers include phosphate, acetate, or carbonate (e.g., $(NH_4)_2CO_3$ or $NaHCO_3$) buffers or any other acid or base, such as ammonia or alkali-metal hydroxides. The concentration range for the initiators and buffers can vary from 0.01% to 5% by weight based on the aqueous polymerization medium.

Typical chain-transfer agents like $H_2$, lower alkanes, alcohols, ethers, esters, and methylene fluoride may be useful in the preparation of the copolymer in some embodiments of the method according to the present disclosure.

Termination primarily via chain-transfer results in a polydispersity of about 2.5 or less. In some embodiments of the method according to the present disclosure, the polymerization is carried out without any chain-transfer agents. A lower polydispersity can sometimes be achieved in the absence of chain-transfer agents. Recombination typically leads to a polydispersity of about 1.5 for small conversions.

Useful polymerization temperatures can range from 40° C. to 150° C. Typically, polymerization is carried out in a temperature range from 40° C. to 120° C., 70° C. to 100° C., or 80° C. to 90° C. The polymerization pressure is usually in the range of 0.8 MPa to 2.5 MPa, 1 MPa to 2.5 MPa, and in some embodiments is in the range from 1.0 MPa to 2.0 MPa. Fluorinated monomers such as HFP can be precharged and fed into the reactor as described, for example, in Modern Fluoropolymers, ed. John Scheirs, Wiley & Sons, 1997, p. 241. Perfluoroalkoxyalkyl allyl ethers represented by formula $CF_2=CFCF_2(OC_nF_{2n})_zORf$, wherein n, z, and $Rf_2$ are as defined above in any of their embodiments, are typically liquids and may be sprayed into the reactor or added directly, vaporized, or atomized.

Conveniently, in the methods of making the copolymer and ionomer according to the present disclosure, the polymerization process may be conducted with no emulsifier (e.g., no fluorinated emulsifier). Surprisingly, we have found that even with the incorporation of liquid perfluoroalkoxyalkyl allyl ethers or bisolefins in larger amounts, no fluorinated emulsifier is needed to ensure proper incorporation of these monomers.

In some embodiments, however, perfluorinated or partially fluorinated emulsifiers may be useful. Generally these fluorinated emulsifiers are present in a range from about 0.02% to about 3% by weight with respect to the polymer. Polymer particles produced with a fluorinated emulsifier typically have an average diameter, as determined by dynamic light scattering techniques, in range of about 10 nanometers (nm) to about 300 nm, and in some embodiments in range of about 50 nm to about 200 nm. Examples of suitable emulsifiers include perfluorinated and partially fluorinated emulsifier having the formula $[R_f-O-L-COO^-]_i X^{i+}$ wherein L represents a linear partially or fully fluorinated alkylene group or an aliphatic hydrocarbon group, Rf represents a linear partially or fully fluorinated aliphatic group or a linear partially or fully fluorinated aliphatic group interrupted with one or more oxygen atoms, $X^{i+}$ represents a cation having the valence i and i is 1, 2 or 3. (See, e.g., U.S. Pat. No. 7,671,112 to Hintzer et al.). Additional examples of suitable emulsifiers also include perfluorinated polyether emulsifiers having the formula $CF_3-(OCF_2)_x-O-CF_2-X'$, wherein x has a value of 1 to 6 and X' represents a carboxylic acid group or salt thereof, and the formula $CF_3-O-(CF_2)_3-(OCF(CF_3)-CF_2)_y-O-L-Y'$ wherein y has a value of 0, 1, 2 or 3, L represents a divalent linking group selected from $-CF(CF_3)-$, $-CF_2-$, and $-CF_2CF_2-$, and Y' represents a carboxylic acid group or salt thereof (See, e.g., U.S. Pat. Publ. No. 2007/0015865 to Hintzer et al.). Other suitable emulsifiers include perfluorinated polyether emulsifiers having the formula $R_f-O(CF_2CF_2O)_xCF_2COOA$ wherein Rf is $C_bF_{(2b+1)}$; where b is 1 to 4, A is a hydrogen atom, an alkali metal or $NH_4$, and x is an integer of from 1 to 3. (See, e.g., U.S. Pat. Publ. No. 2006/0199898 to Funaki et al.). Suitable emulsifiers also include perfluorinated emulsifiers having the formula $F(CF_2)_bO(CF_2CF_2O)_xCF_2COOA$ wherein A is a hydrogen atom, an alkali metal or $NH_4$, b is an integer of from 3 to 10, and x is 0 or an integer of from 1 to 3. (See, e.g., U.S. Pat. Publ. No. 2007/0117915 to Funaki et al.). Further suitable emulsifiers include fluorinated polyether emulsifiers as described in U.S. Pat. No. 6,429,258 to Morgan et al. and perfluorinated or partially fluorinated alkoxy acids and salts thereof wherein the perfluoroalkyl component of the perfluoroalkoxy has 4 to 12 carbon atoms, or 7 to 12 carbon atoms. (See, e.g., U.S. Pat. No. 4,621,116 to Morgan). Suitable emulsifiers also include partially fluorinated polyether emulsifiers having the formula $[R_f-(O)_t-CHF-(CF_2)_x-COO-]_i X^{i+}$ wherein $R_f$ represents a partially or fully fluorinated aliphatic group optionally interrupted with one or more oxygen atoms, t is 0 or 1 and x is 0 or 1, $X^{i+}$ represents a cation having a valence i and i is 1, 2 or 3. (See, e.g., U.S. Pat. Publ. No. 2007/0142541 to Hintzer et al.). Further suitable emulsifiers include perfluorinated or partially fluorinated ether-containing emulsifiers as described in U.S. Pat. Publ. Nos. 2006/0223924, 2007/0060699, and 2007/0142513 each to Tsuda et al. and 2006/0281946 to Morita et al. Conveniently, in some embodiments, the method of making the copolymer according to the present disclosure may be conducted in the absence of any of these emulsifiers or any combination thereof, for example, using the methods found in U.S. Pat. Publ. No. 2007/0149733 (Otsuka).

If fluorinated emulsifiers are used, the emulsifiers can be removed or recycled from the fluoropolymer latex, if desired, as described in U.S. Pat. No. 5,442,097 to Obermeier et al., U.S. Pat. No. 6,613,941 to Felix et al., U.S. Pat. No. 6,794,550 to Hintzer et al., U.S. Pat. No. 6,706,193 to Burkard et al., and U.S. Pat. No. 7,018,541 to Hintzer et al.

The polymerization can be carried out without adding any perfluorinated alkanoic acids, in particular perfluorinated alkanoic acids with 6 to 14 carbon atoms, and in particular with 8 carbon atoms (perfluorinated octanoic acid (PFOA)) to the reaction mixture. Perfluorinated alkanoic acids represented by formula $Rf-(CF_2)_n-A$, wherein Rf is a perfluorinated alkyl radical that only contains F and C atoms, n is an integer of 5 to 14 and A is an acid anion salt, for example a $-COO^-X$ wherein X is $H^+$, or a cationic salt such as $NH_4^+$ or $Na^+$ another metal salt, have become under increased scrutiny because of their environmental persistence and bioaccumulation. Therefore, their use is avoided. However, even if no such emulsifiers are used in the preparation of the polymers, they may be generated in situ in certain reactions. As another advantage, the copolymers made by the methods of the present disclosure may have a very low extractable amount of perfluorinated alkanoic acids, for example amounts of less than 100 ppb based on the weight of $C_6-C_{12}$, preferably $C_6$ to $C_{14}$ perfluorinated alkanoic acids, and may have an amount of extractable octanoic acid ($C_8$) of less than 50 ppb, preferably less than 30 ppb—based on the weight of the polymer.

In some embodiments, the obtained copolymer or ionomer latices are purified by at least one of anion- or cation-exchange processes to remove functional comonomers, anions, and/or cations before coagulation or spray drying (described below). As used herein, the term "purify" refers to at least partially removing impurities, regardless of whether the removal is complete. The obtained copolymer dispersion after aqueous emulsion polymerization and optional ion-exchange purification can be used as is or, if higher solids are desired, can be upconcentrated.

To coagulate the obtained copolymer latex, any coagulant which is commonly used for coagulation of a fluoropolymer latex may be used, and it may, for example, be a water-soluble salt (e.g., calcium chloride, magnesium chloride, aluminum chloride or aluminum nitrate), an acid (e.g., nitric acid, hydrochloric acid or sulfuric acid), or a water-soluble organic liquid (e.g., alcohol or acetone). The amount of the coagulant to be added may be in a range of 0.001 to 20 parts by mass, for example, in a range of 0.01 to 10 parts by mass per 100 parts by mass of the latex. Alternatively or additionally, the latex may be frozen for coagulation or mechanically coagulated, for example, with a homogenizer as described in U.S. Pat. No. 5,463,021 (Beyer et al.). Alternatively or additionally, the latex may be coagulated by adding polycations. It may also be useful to avoid acids and alkaline earth metal salts as coagulants to avoid metal contaminants. To avoid coagulation altogether and any contaminants from coagulants, spray drying the latex after polymerization and optional ion-exchange purification may be useful to provide solid copolymer.

A coagulated copolymer can be collected by filtration and washed with water. The washing water may, for example, be ion-exchanged water, pure water, or ultrapure water. The amount of the washing water may be from 1 to 5 times by mass to the copolymer, whereby the amount of the emulsifier attached to the copolymer can be sufficiently reduced by one washing.

In some embodiments of the methods of making the copolymer or ionomer according to the present disclosure, radical polymerization also can be carried out by suspension polymerization. Suspension polymerization will typically produce particle sizes up to several millimeters.

Fluoropolymers obtained by aqueous emulsion polymerization with inorganic initiators (e.g. persulfates, $KMnO_4$, etc.) typically have a high number of unstable carbon-based end groups (e.g. more than 200 —COOM or —COF end groups per $10^6$ carbon atoms, wherein M is hydrogen, a metal cation, or $NH_2$). These carbonyl end groups are vulnerable to peroxide radical attacks, which reduce the oxidative stability of the fluorinated ionomers. The number of unstable end groups can be determined by Fourier-transform infrared spectroscopy.

Post-fluorination with fluorine gas is commonly used to cope with unstable end groups and any concomitant degradation. Post-fluorination of the fluoropolymer can convert —COOH, amide, hydride, —COF, and other nonperfluorinated end groups or —CF=$CF_2$ to —$CF_3$ end groups. The post-fluorination may be carried out in any convenient manner. The post-fluorination can be conveniently carried out with nitrogen/fluorine gas mixtures in ratios of 75-90:25-10 at temperatures between 20° C. and 250° C., in some embodiments in a range of 150° C. to 250° C. or 70° C. to 120° C., and pressures from 100 KPa to 1000 KPa. Reaction times can range from about four hours to about 16 hours. Under these conditions, most unstable carbon-based end groups are removed, whereas any —$SO_2X$ groups mostly survive and are converted to —$SO_2F$ groups. In some embodiments, post-fluorination is not carried out when non-fluorinated monomers described above are used as monomers in the polymerization.

The copolymer prepared according to the methods of the present disclosure can be essentially free of copolymerized units derived from a perfluorinated alkyl vinyl ether [e.g., perfluoromethyl vinyl ether ($CF_2$=$CFOCF_3$), perfluoroethyl vinyl ether ($CF_2$=$CFOCF_2CF_3$), and perfluoropropyl vinyl ether ($CF_2$=$CFOCF_2CF_2CF_3$)] and perfluoroalkoxyalkyl vinyl ethers. "Essentially free" as used herein is referred to an amount of 0 to 0.9% by weight, in some embodiments from 0 to 0.1% by weight. The copolymers prepared by the methods of the present disclosure can be prepared without using any vinyl ethers, although minor amounts of vinyl ethers present as impurities may be tolerated. Examples of perfluoroalkoxyalkyl vinyl ethers that may be avoided include $CF_2$=$CFOCF_2OCF_3$, $CF_2$=$CFOCF_2OCF_2CF_3$, $CF_2$=$CFOCF_2CF_2OCF_3$, $CF_2$=$CFOCF_2CF_2CF_2OCF_3$, $CF_2$=$CFOCF_2CF_2CF_2CF_2OCF_3$, $CF_2$=$CFOCF_2CF_2OCF_2CF_3$, $CF_2$=$CFOCF_2CF_2CF_2OCF_2CF_3$, $CF_2$=$CFOCF_2CF_2CF_2CF_2OCF_2CF_3$, $CF_2$=$CFOCF_2CF_2OCF_2OCF_3$, $CF_2$=$CFOCF_2CF_2OCF_2CF_2OCF_3$, $CF_2$=$CFOCF_2CF_2OCF_2CF_2CF_2OCF_3$, $CF_2$=$CFOCF_2CF_2OCF_2CF_2CF_2CF_2OCF_3$, $CF_2$=$CFOCF_2CF_2OCF_2CF_2CF_2CF_2CF_2OCF_3$, $CF_2$=$CFOCF_2CF_2(OCF_2)_3OCF_3$, $CF_2$=$CFOCF_2CF_2(OCF_2)_4OCF_3$, $CF_2$=$CFOCF_2CF_2OCF_2OCF_2OCF_3$, $CF_2$=$CFOCF_2CF_2OCF_2CF_2CF_3$, $CF_2$=$CFOCF_2CF_2OCF_2CF_2OCF_2CF_3$, $CF_2$=$CFOCF_2CF(CF_3)$—O—$C_3F_7$ (PPVE-2), $CF_2$=$CF(OCF_2CF(CF_3))_2$—O—$C_3F_7$ (PPVE-3), and $CF_2$=$CF(OCF_2CF(CF_3))_3$—O—$C_3F_7$ (PPVE-4).

Vinyl ethers can undergo termination reactions (e.g. cleavage of vinyl ether) during polymerization, in particular at higher temperatures, and creating unstable carboxy-endgroups.

We have found that fluorinated copolymers made with perfluorinated allyl ether monomers can advantageously be produced, for example, by aqueous emulsion polymerization at higher temperatures (e.g., higher than 70° C. or 80° C.) than fluorinated copolymers made with corresponding perfluorinated vinyl ether monomers.

SOME EMBODIMENTS OF THE DISCLOSURE

In a first embodiment, the present disclosure provides a method of making a compound comprising at least one perfluorinated allyl ether group, the method comprising:
combining first components comprising:
at least one of $CF_2$=CF—$CF_2$—$OSO_2Cl$ or $CF_2$=CF—$CF_2$—$OSO_2CF_3$,
a polyfluorinated compound comprising at least one ketone, carboxylic acid halide, or a combination thereof, and
fluoride ion
to provide the compound comprising at least one perfluorinated allyl ether group.

In a second embodiment, the present disclosure provides the method of the first embodiment, wherein the compound comprising at least one perfluorinated allyl ether group is represented by formula $CF_2$=$CFCF_2(OC_nF_{2n})_z$ORf, wherein each n is independently from 2 to 6, z is 0, 1, or 2, and Rf is a linear or branched perfluoroalkyl group having from 1 to 8 carbon atoms and optionally interrupted by one or more —O— groups.

In a third embodiment, the present disclosure provides the method of the second embodiment, wherein z is 0, and wherein Rf is a linear or branched perfluoroalkyl group having from 1 to 4 carbon atoms.

In a fourth embodiment, the present disclosure provides the method of the first embodiment, wherein the compound comprising at least one perfluorinated allyl ether group is represented by formula $CF_2$=CF—$CF_2$—O—$R_F$—O—$CF_2$—CF=$CF_2$, wherein $R_F$ represents linear or branched perfluoroalkylene or perfluoropolyoxyalkylene or arylene, which may be non-fluorinated or fluorinated.

In a fifth embodiment, the present disclosure provides the method of the fourth embodiment, wherein $R_F$ represents linear or branched perfluoroalkylene or perfluoropolyoxyalkylene.

In a sixth embodiment, the present disclosure provides the method of the first embodiment, wherein the polyfluorinated compound comprising at least one ketone or carboxylic acid halide is ketone O=$CR^3R^3$, wherein each $R^3$ is independently a linear or branched perfluoroalkyl group having from 1 to 12 carbon atoms that is optionally terminated by —$SO_2F$, —$OCF_2CF$=$CF_2$, —COF, —$CF(CF_3)_2$—$CF_2CO_2H$, —F, —Cl, —Br, —I, CN, or —$CO_2$-alkyl, and optionally interrupted by one or more —O— groups.

In a seventh embodiment, the present disclosure provides the method of the first embodiment, wherein the polyfluorinated compound comprising at least one ketone or carboxylic acid halide is carboxylic acid fluoride FC(O)($R^1$) or FC(O)($R^2$), wherein $R^1$ is a linear or branched perfluoroalkyl group having from 2 to 12 carbon atoms that is optionally terminated by —$SO_2F$, —$OCF_2CF$=$CF_2$, —COF, —Cl, —Br, —I, or —$CO_2$-alkyl, and wherein $R^2$ is a linear or branched perfluoroalkyl group having from 2 to 14 carbon atoms that is interrupted by one or more ether —O— groups and optionally terminated by —$SO_2F$, —$OCF_2CF$=$CF_2$, —COF, —Cl, —Br, —I, or —$CO_2$-alkyl.

In an eighth embodiment, the present disclosure provides the method of any one of the first to fifth embodiments, wherein the carboxylic acid halide is a carboxylic acid fluoride.

In a ninth embodiment, the present disclosure provides the method of any one of the first to eighth embodiments, wherein the fluoride ion is introduced from at least one of sodium fluoride, potassium fluoride, rubidium fluoride, cesium fluoride, or (R)$_4$NF, wherein is each R is independently alkyl having from 1 to 6 carbon atoms.

In a tenth embodiment, the present disclosure provides the method of any one of the first to ninth embodiments, wherein the first components comprise $CF_2$=CF—$CF_2$—$OSO_2Cl$.

In an eleventh embodiment, the present disclosure provides the method of the tenth embodiment, further comprising combining second components comprising B($OSO_2Cl$)$_3$ and hexafluoropropylene to provide $CF_2$=CF—$CF_2$—$OSO_2Cl$.

In a twelfth embodiment, the present disclosure provides a method of making $CF_2$=CF—$CF_2$—$OSO_2Cl$, the method comprising:
combining second components comprising B($OSO_2Cl$)$_3$ and hexafluoropropylene to provide $CF_2$=CF—$CF_2$—$OSO_2Cl$.

In a thirteenth embodiment, the present disclosure provides the method of the eleventh or twelfth embodiment, wherein the second components further comprise a non-aromatic solvent.

In a fourteenth embodiment, the present disclosure provides the method of any one of the eleventh to thirteenth embodiments, further comprising:
combining third components comprising $BCl_3$ and $ClSO_3H$ to provide B($OSO_2Cl$)$_3$.

In a fifteenth embodiment, the present disclosure provides a compound represented by formula $CF_2$=CF—$CF_2$—$OSO_2Cl$.

In a sixteenth embodiment, the present disclosure provides the method of any one of the first to ninth embodiments, wherein the first components comprise $CF_2$=CF—$CF_2$—$OSO_2CF_3$.

In a seventeenth embodiment, the present disclosure provides the method of the sixteenth embodiment, further comprising combining second components comprising M($OSO_2CF_3$)$_3$ and hexafluoropropylene to provide $CF_2$=CF—$CF_2$—$OSO_2CF_3$, wherein M is Al or B.

In an eighteenth embodiment, the present disclosure provides the method of the seventeenth embodiment, wherein the second components are combined at a temperature between 0° C. and 90° C.

In a nineteenth embodiment, the present disclosure provides a method of making $CF_2$=CF—$CF_2$—$OSO_2CF_3$, the method comprising combining second components comprising M($OSO_2CF_3$)$_3$ and hexafluoropropylene at a temperature above 0° C. to provide $CF_2$=CF—$CF_2$—$OSO_2CF_3$, wherein M is Al or B.

In a twentieth embodiment, the present disclosure provides the method of any one of the seventeenth to nineteenth embodiments, further comprising combining the $CF_2$=CF—$CF_2$—$OSO_2CF_3$ with water at a temperature between 8° C. and 28° C.

In a twenty-first embodiment, the present disclosure provides a method of any one of the seventeenth to twentieth embodiments, wherein M is B.

In a twenty-second embodiment, the present disclosure provides the method of the twenty-first embodiments, wherein the second components are combined at a temperature between 2° C. and 10° C.

In a twenty-third embodiment, the present disclosure provides the method of any one of the seventeenth to twentieth embodiments, wherein M is Al.

In a twenty-fourth embodiment, the present disclosure provides the method of any one of the first to fourteenth and sixteenth to twenty-third embodiments, further comprising combining the compound comprising at least one perfluorinated allyl ether group with at least one partially fluorinated or perfluorinated ethylenically unsaturated monomer represented by formula $R^aCF$=$CR^a{}_2$, wherein each W is independently fluoro, chloro, bromo, hydrogen, a fluoroalkyl group, alkyl having up to 10 carbon atoms, alkoxy having up to 8 carbon atoms, or aryl having up to 8 carbon atoms.

The following specific, but non-limiting, examples will serve to illustrate the present disclosure.

EXAMPLES

All materials are commercially available, for example from Sigma-Aldrich Chemical Company, Milwaukee, Wis., USA, or known to those skilled in the art, unless otherwise stated or apparent.

The following abbreviations are used in this section: mL=milliliters, g=grams, mmHg=millimeters of mercury, min=minutes, h=hours, NMR=nuclear magnetic resonance, ppm=parts per million, r.t.=room temperature, mol=moles, mmol=millimoles, ° C.=degrees Celsius, MHz=Megahertz. Abbreviations for materials used in this section, as well as descriptions of the materials, are provided in Table 1.

Materials

TABLE 1

| Material | Details |
| --- | --- |
| Chlorosulfonic acid | $ClSO_3H$, 99%, available from Sigma-Aldrich |
| 1,4-bis(carbonylfluoride)perfluorobutane | May be prepared as described in Example 4 of PCT patent application WO16/089617 |
| $BCl_3$ | 99.8%, available from abcr GmbH, Karlsruhe, Germany |
| $FSO_3H$ | Purified by triple distillation, available from Sigma-Aldrich |

TABLE 1-continued

| Material | Details |
|---|---|
| $CH_2Cl_2$ | ≥99.9%, available from CARL ROTH, Karlsruhe, Germany, under the trade designation "ROTISOLV PESTILYSE plus" |
| $CF_3SO_3H$ | 98%, available from Sigma-Aldrich |
| $Na_2SO_4$ | >99%, available from CARL ROTH |
| KF | >99% p.a., available from CARL ROTH |
| Diglyme | 99%, stab. with 100 ppm BHT, available from abcr GmbH |
| Freon-113 | >99%, "puriss. p.a.", available from Fluka AG |

Example 1 (EX-1): Synthesis of $B(OSO_2Cl)_3$

To a 100 mL three-necked flask equipped with a cold finger condenser, addition funnel and thermometer, 31.9 g (0.27 mol) of $BCl_3$ was condensed and afterwards chlorosulfonic acid (68.0 g, 0.58 mol) was dropwise added so that the temperature did not exceed 6-7° C. Afterwards, the viscous substance was stirred 2 h at 10° C. and was slowly warmed up to r.t. and was stirred at this temperature for 2 h. Then, all volatiles were removed in vacuo within 45 min. During this process, the reaction mixture crystallized and $B(OSO_2Cl)_3$ was obtained in quantitative yield as a white powder which was further used without additional purification.

$^{11}B$ NMR (128 MHz, $CDCl_3$): δ −6.71 (bs, $BO_3$, 1B)

Example 2 (EX-2): Synthesis of $CF_2$=CF—$CF_2$—$OSO_2Cl$ (PFAClS)

$B(OSO_2Cl)_3$ (3.13 g, 8.8 mmol), prepared as described in EX-1, was suspended in $CH_2Cl_2$ (50 mL) in a 100 mL Schlenk flask. To this suspension, HFP (4.91 g, 32.7 mmol) was condensed. The reaction mixture was warmed up to 15° C. and was stirred at this temperature for 3 h and then at r.t. for 18 h. At this temperature, the reaction mixture changed its color and became homogenous. Gaseous products were slowly removed, cold water (60 mL) was added to the reaction mixture which was stirred for 60 min. The bottom layer was separated, washed with water (2×30 mL) and dried over $Na_2SO_4$. PFAClS was obtained in 56% NMR yield (1.2 g, 4.9 mmol).

$^{19}F$ NMR (376 MHz, $CDCl_3$): δ −72.0 (m, $CF_2$, 2F), −87.7 (ddt, $^2J_{FF}$=46 Hz, $^{cis}J_{FF}$=38 Hz, $^4J_{FF}$=9 Hz, CF, 1F), −101.7 (ddt, $^2J_{FF}$=46 Hz, $^{trans}J_{FF}$=118 Hz, $^4J_{FF}$=28 Hz, CF, 1F), −190.2 (ddt, $^{cis}J_{FF}$=38 Hz, $^{trans}J_{FF}$=118 Hz, $^3J_{FF}$=14 Hz, CF, 1F).

Example 3 (EX-3): Synthesis of $CF_2$=CF—$CF_2$—$OSO_2Cl$ (PFAClS)

Into a 100-mL glass ampoule $B(OSO_2Cl)_3$ (10.1 g, 28 mmol), prepared as described in EX-1, and Freon-113 (20 mL) were placed. Next, HFP (13.1 g, 87 mmol) was condensed using a gas line and then the reaction mixture was warmed to 0-4° C. Then, the reaction mixture was stirred for 2 h at this temperature and 10 h at r.t. After degassing, the volatiles were recondensed into a Schlenk flask. PFAClS was obtained in 35% NMR yield (2.4 g, 9.7 mmol).

Example 4 (EX-4): Synthesis of $B(OSO_2CF_3)_3$

Into a 250 mL three-necked flask equipped with a cold finger condenser, addition funnel and thermometer, $BCl_3$ (49.2 g, 0.42 mol) was condensed and afterwards $CF_3SO_3H$ (133.5 g, 0.89 mol) was dropwise added so that the temperature did not exceed 10° C. After termination, the viscous reaction mixture was stirred 2 h at 10° C. and the temperature was slowly warmed up to r.t. and stirred at this temperature for 2 h. All volatiles were removed in vacuo. During this process the reaction mixture crystallized $B(OSO_2CF_3)_3$ was obtained in quantitative yield as a white powder.

$^{19}F$ NMR (376 MHz, $CD_2Cl_2$): δ −74.51 (s, $CF_3SO_2$, 3F)
$^{11}B$ NMR (128 MHz, $CD_2Cl_2$): δ −1.26 (bs, $BO_3$, 1B)

Example 5 (EX-5): Synthesis of $CF_2$=CF—$CF_2$—$OSO_2CF_3$ (PFAOTf)

$B(OSO_2CF_3)_3$ (16.3 g, 36 mmol), prepared as described for EX-4, was placed into a 250 mL glass ampoule. Afterwards, HFP (16.7 g, 111 mmol) was condensed. The ampoule was warmed to 0-4° C. and the reaction mixture was stirred for 4 h at 4° C. and 1 hr at 5-8° C. All volatiles were degassed. The residue was recondensed, crude colorless liquid (24.3 g) was collected and mixed with water (27 mL) at 25-27° C. for 30 min. In case the temperature exceeded 27° C., ice was added. The organic phase was separated and dried over $Na_2SO_4$. The crude product (9.7 g) was distilled using a short Vigreux column. The main fraction boiled at 81-83° C./760 mmHg. PFAOTf was obtained in 75% yield (7.5 g, 27 mmol). $^{19}F$ NMR (376 MHz, $CDCl_3$): δ −68.4 (m, $CF_2$, 2F), −74.1 (t, $^5J_{FF}$=6 Hz, $CF_3$, 3F), −88.6 (ddt, $^2J_{FF}$=45 Hz, $^{cis}J_{FF}$=39 Hz, $^4J_{FF}$=7 Hz, CF, 1F), −102.6 (ddt, $^2J_{FF}$=45 Hz, $^{trans}J_{FF}$=117 Hz, $^4J_{FF}$=27 Hz, CF, 1F), −190.4 (ddt, $^{cis}J_{FF}$=39 Hz, $^{trans}J_{FF}$=117 Hz, $^3J_{FF}$=14 Hz, CF, 1F)

Example 6 (EX-6): Synthesis of $CF_2$=CF—$CF_2$—O—$(CF_2)_4$—O—$CF_2$—CF=$CF_2$

A suspension of KF (0.22, 3.8 mmol) and diglyme (5 mL) was stirred for 30 min at r.t. in a 50-mL Schlenk flask. Perfluorobutane 1,4-bis(carbonyl fluoride) (0.8 g, 4.1 mmol) was added and the reaction mixture was stirred at 4° C. for 1 h (formation of a clear solution). At this temperature, PFAOTf (1.06 g, 3.8 mmol), prepared as in EX-5, was dropwise added. The reaction mixture was stirred 4 h at 5° C., 12 h at r.t. and the formation of a yellowish emulsion was observed. The reaction mixture was diluted with cold water (30 mL), the organic phase was separated, washed with water (10 mL) and dried over sodium sulfate. $CF_2$=CF—$CF_2$—O—$(CF_2)_4$—O—$CF_2$—CF=$CF_2$ was obtained in 30% NMR yield.

$^{19}$NMR (376 MHz, $CDCl_3$): δ −71.5 (m, $OCF_2$, 4F), −83.9 (t, $^3J_{FF}$=12 Hz, $OCF_2$, 4F), −90.9 (ddt, $^2J_{FF}$=54 Hz, $^{cis}J_{FF}$=39 Hz, $^4J_{FF}$=7 Hz, CF, 2F), −104.2 (ddt, $^2J_{FF}$=54 Hz, $^{trans}J_{FF}$=117 Hz, $^4J_{FF}$=25 Hz, CF, 2F), −119.6 (t, $^3J_{FF}$=9 Hz, $CF_2$, 4F), −190.2 (ddt, $^{cis}J_{FF}$=39 Hz, $^{trans}J_{FF}$=117 Hz, $^3J_{FF}$=15 Hz, CF, 2F) $^{13}C$ NMR (101 MHz, $CDCl_3$): δ 153.9 (tdt, $^1J_{CF}$=294 Hz, $^2J_{CF}$=40 Hz, $^3J_{CF}$=2 Hz, =$CF_2$, 2C), 121.2 (dm, $^1J_{CF}$=242 Hz, $^2J_{CF}$=24 Hz, $^3J_{CF}$=3 Hz, =CF, 2C), 117.0 (tdt, $^1J_{CF}$=272 Hz, $^2J_{CF}$=30 Hz, $^3J_{CF}$=7 Hz, $OCF_2$, 2C), 115.7 (tt, $^1J_{CF}$=288 Hz, $^2J_{CF}$=32 Hz, $OCF_2$, 2C), 108.4 (tsep, $^1J_{CF}$=268 Hz, $^2J_{CF}$=35 Hz, $CF_2$, 2C)

Various modifications and alterations of this disclosure may be made by those skilled in the art without departing from the scope and spirit of the disclosure, and it should be understood that this invention is not to be unduly limited to the illustrative embodiments set forth herein.

What is claimed is:

1. A method of making a compound comprising at least one perfluorinated allyl ether group, the method comprising:
combining first components comprising:

$$CF_2=CF-CF_2-OSO_2Cl,$$

a polyfluorinated compound comprising at least one ketone, carboxylic acid halide, or a combination thereof, and
fluoride ion
to provide the compound comprising at least one perfluorinated allyl ether group.

2. The method of claim 1, wherein the compound comprising at least one perfluorinated allyl ether group is represented by formula $CF_2=CFCF_2(OC_nF_{2n})_zORf$, wherein each n is independently from 2 to 6, z is 0, 1, or 2, and Rf is a linear or branched perfluoroalkyl group having from 1 to 8 carbon atoms and optionally interrupted by one or more —O— groups.

3. The method of claim 1, wherein the compound comprising at least one perfluorinated allyl ether group is represented by formula $CF_2=CF-CF_2-O-R_F-O-CF_2-CF=CF_2$, wherein $R_F$ represents linear or branched perfluoroalkylene or perfluoropolyoxyalkylene or arylene, which may be non-fluorinated or fluorinated.

4. The method of claim 3, wherein $R_F$ represents linear or branched perfluoroalkylene or perfluoropolyoxyalkylene.

5. The method of claim 1, wherein the polyfluorinated compound is $O=CR^3R^3$, wherein each $R^3$ is independently a linear or branched perfluoroalkyl group having from 1 to 12 carbon atoms that is optionally terminated by —$SO_2F$, —$OCF_2CF=CF_2$, —COF, —$CF(CF_3)_2$, —$CF_2CO_2H$, —F, —Cl, —Br, —I, —CN, or —$CO_2$-alkyl, and optionally interrupted by one or more —O— groups.

6. The method of claim 1, wherein the polyfluorinated compound is $FC(O)(R^1)$ or $FC(O)(R^2)$, wherein $R^1$ is a linear or branched perfluoroalkyl group having from 2 to 12 carbon atoms that is optionally terminated by —$SO_2F$, —$OCF_2CF=CF_2$, —COF, —Cl, —Br, —I, or —$CO_2$-alkyl, and wherein $R^2$ is a linear or branched perfluoroalkyl group having from 2 to 14 carbon atoms that is interrupted by one or more —O— groups and optionally terminated by —$SO_2F$, —$OCF_2CF=CF_2$, —COF, —Cl, —Br, —I, or —$CO_2$-alkyl.

7. The method claim 1, wherein the fluoride ion is comprised in at least one of sodium fluoride, potassium fluoride, rubidium fluoride, cesium fluoride, or $(R)_4NF$, wherein is each R is independently alkyl having from 1 to 6 carbon atoms.

8. The method of claim 1, further comprising combining second components comprising $B(OSO_2Cl)_3$ and hexafluoropropylene to provide $CF_2=CF-CF_2-OSO_2Cl$.

9. A method of making $CF_2=CF-CF_2-OSO_2Cl$, the method comprising:
combining second components comprising $B(OSO_2Cl)_3$ and hexafluoropropylene to provide $CF_2=CF-CF_2-OSO_2Cl$.

10. The method of claim 9, further comprising:
combining third components comprising $BCl_3$ and $ClSO_3H$ to provide $B(OSO_2Cl)_3$.

11. A compound represented by formula $CF_2=CF-CF_2-OSO_2Cl$.

12. The method of claim 2, wherein z is 0, and wherein Rf is a linear or branched perfluoroalkyl group having from 1 to 4 carbon atoms.

13. The method of claim 1, further comprising combining and interpolymerizing the compound comprising at least one perfluorinated allyl ether group with at least one partially fluorinated or perfluorinated ethylenically unsaturated monomer represented by formula $R^aCF=CR^a_2$, wherein each $R^a$ is independently fluoro, chloro, bromo, hydrogen, a fluoroalkyl group, alkyl having up to 10 carbon atoms, alkoxy having up to 8 carbon atoms, or aryl having up to 8 carbon atoms to form a fluoropolymer.

14. A method of making a compound comprising at least one perfluorinated allyl ether group, the method comprising:
combining first components comprising:

$$CF_2=CF-CF_2-OSO_2CF_3,$$

a polyfluorinated compound comprising at least one carboxylic acid halide, and
fluoride ion
to provide the compound comprising at least one perfluorinated allyl ether group.

15. The method of claim 14, wherein the compound comprising at least one perfluorinated allyl ether group is represented by formula $CF_2=CFCF_2(OC_nF_{2n})_zORf$, wherein each n is independently from 2 to 6, z is 0, 1, or 2, and Rf is a linear or branched perfluoroalkyl group having from 1 to 8 carbon atoms and optionally interrupted by one or more —O— groups.

16. The method of claim 15, wherein z is 0, and wherein Rf is a linear or branched perfluoroalkyl group having from 1 to 4 carbon atoms.

17. The method of claim 14, wherein the compound comprising at least one perfluorinated allyl ether group is represented by formula $CF_2=CF-CF_2-O-R_F-O-CF_2-CF=CF_2$, wherein $R_F$ represents linear or branched perfluoroalkylene or perfluoropolyoxyalkylene or arylene, which may be non-fluorinated or fluorinated.

18. The method of claim 14, wherein the polyfluorinated compound comprising at least one carboxylic acid halide is $FC(O)(R^1)$ or $FC(O)(R^2)$, wherein $R^1$ is a linear or branched perfluoroalkyl group having from 2 to 12 carbon atoms that is optionally terminated by —$SO_2F$, —$OCF_2CF=CF_2$, —COF, —Cl, —Br, —I, or —$CO_2$-alkyl, and wherein $R^2$ is a linear or branched perfluoroalkyl group having from 2 to 14 carbon atoms that is interrupted by one or more —O— groups and optionally terminated by —$SO_2F$, —$OCF_2CF=CF_2$, —COF, —Cl, —Br, —I, or —$CO_2$-alkyl.

* * * * *

UNITED STATES PATENT AND TRADEMARK OFFICE
CERTIFICATE OF CORRECTION

PATENT NO. : 11,292,763 B2
APPLICATION NO. : 16/613900
DATED : April 5, 2022
INVENTOR(S) : Klaus Hintzer et al.

Page 1 of 1

It is certified that error appears in the above-identified patent and that said Letters Patent is hereby corrected as shown below:

In the Claims

Column 23
Line 52, In Claim 7, after "wherein", delete "is".

Signed and Sealed this
Sixteenth Day of May, 2023

Katherine Kelly Vidal
*Director of the United States Patent and Trademark Office*